United States Patent [19]
Saringer

[11] Patent Number: 5,895,418
[45] Date of Patent: *Apr. 20, 1999

[54] DEVICE FOR PRODUCING COLD THERAPY

[75] Inventor: John H. Saringer, Unionville, Canada

[73] Assignee: Saringer Research Inc., Markham

[*] Notice: This patent is subject to a terminal disclaimer.

[21] Appl. No.: 08/803,939

[22] Filed: Feb. 20, 1997

Related U.S. Application Data

[63] Continuation-in-part of application No. 08/316,352, Sep. 30, 1994, Pat. No. 5,628,769.
[60] Provisional application No. 60/014,451, Apr. 1, 1996.
[51] Int. Cl.$^6$ .................................................. A61F 7/02
[52] U.S. Cl. .................................................. 607/104
[58] Field of Search ........................ 607/96–98, 104, 607/107–112, 114; 165/46; 126/204

[56] References Cited

U.S. PATENT DOCUMENTS

| | | |
|---|---|---|
| 3,132,688 | 5/1964 | Nowak . |
| 3,154,926 | 11/1964 | Hirschhorn . |
| 3,888,259 | 6/1975 | Milley . |
| 3,967,627 | 7/1976 | Brown . |
| 4,094,357 | 6/1978 | Sgroi . |
| 4,170,998 | 10/1979 | Sauder . |
| 4,459,468 | 7/1984 | Bailey . |
| 4,523,594 | 6/1985 | Kuznetz . |
| 4,741,338 | 5/1988 | Miyamae . |
| 4,962,761 | 10/1990 | Golden . |
| 5,097,829 | 3/1992 | Quisenberry . |
| 5,174,285 | 12/1992 | Fontenot . |
| 5,269,369 | 12/1993 | Faghri . |
| 5,628,769 | 5/1997 | Saringer ................................. 607/98 |

FOREIGN PATENT DOCUMENTS

| | | |
|---|---|---|
| 0342676 | 11/1989 | European Pat. Off. . |
| 2579888 | 10/1986 | France . |

*Primary Examiner*—Jeffrey R. Jastrazab
*Assistant Examiner*—Ryan Carter
*Attorney, Agent, or Firm*—Lynn Schumacher; Hill & Schumacher; Dowell & Dowell, P.C.

[57] ABSTRACT

The present invention provides heat exchange devices for heating and/or cooling parts of the body for therapeutic treatment of injury. The heat exchange devices include a cooling module with a housing enclosing a cooling chamber. A thermoelectric Peltier unit has a cooled surface sealed against an opening in the housing and a pump is provided for pumping heat exchange fluid through the cooling chamber directly into contact with the cooled surface and through conduits to a patient blanket. A reservoir containing refrigerant is in flow communication with the chamber in the cooling module housing and refrigerant only flows into the housing when depleted from the recirculation flow path between the cooling module and the blanket. Another device uses a thermoelectric unit disposed between two water pumps each of which pumps water to different sections of a flexible water bag which is strapped to the affected area of the user. Water pumped over one side of the thermoelectric unit is heated and water pumped over the other side is cooled.

47 Claims, 18 Drawing Sheets

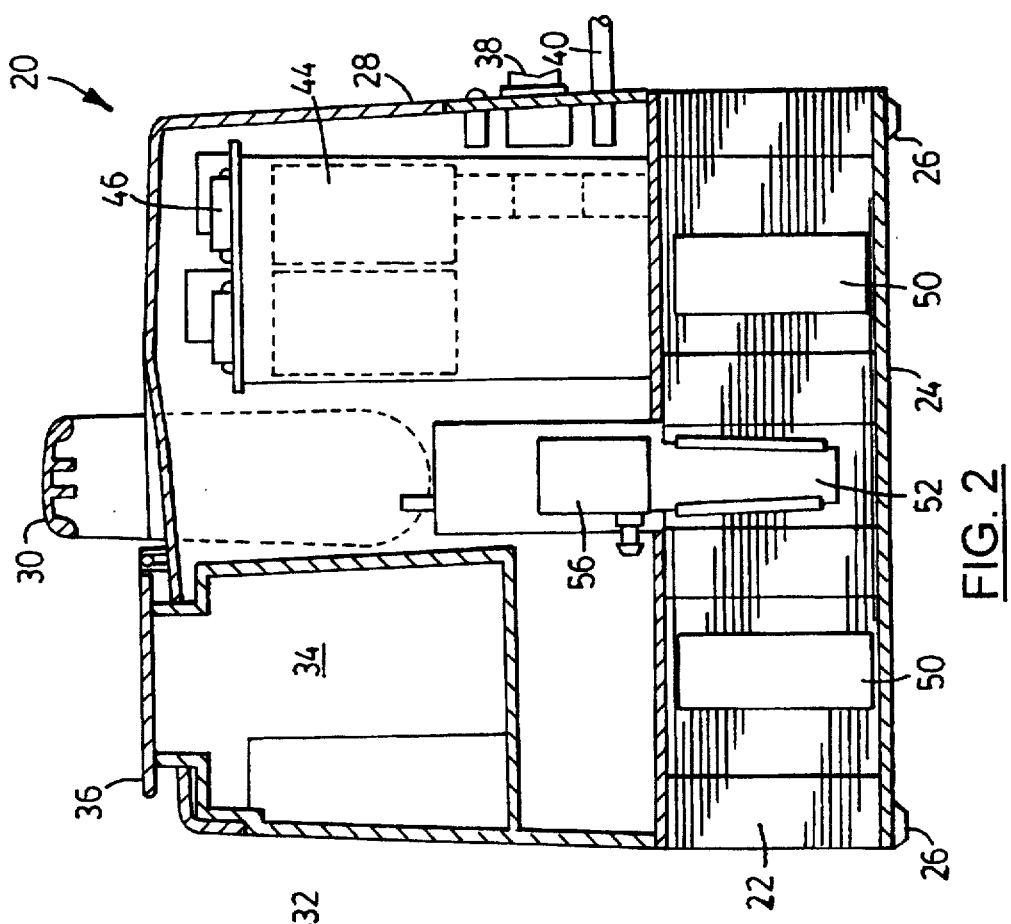
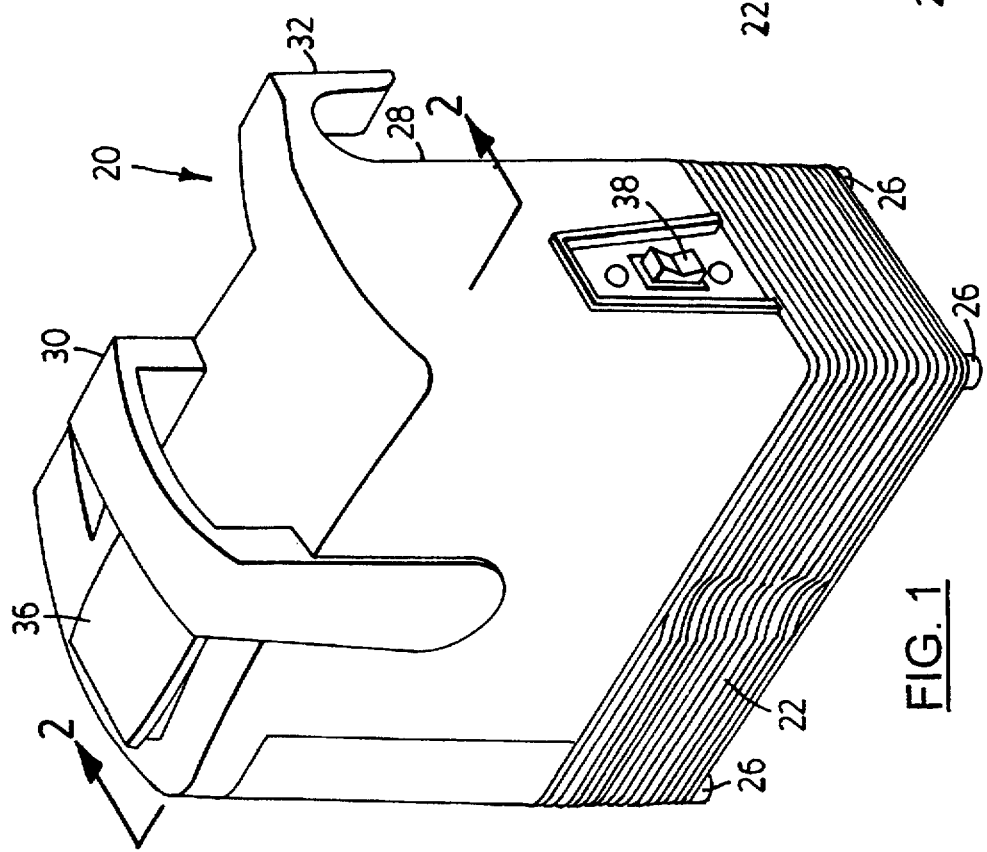

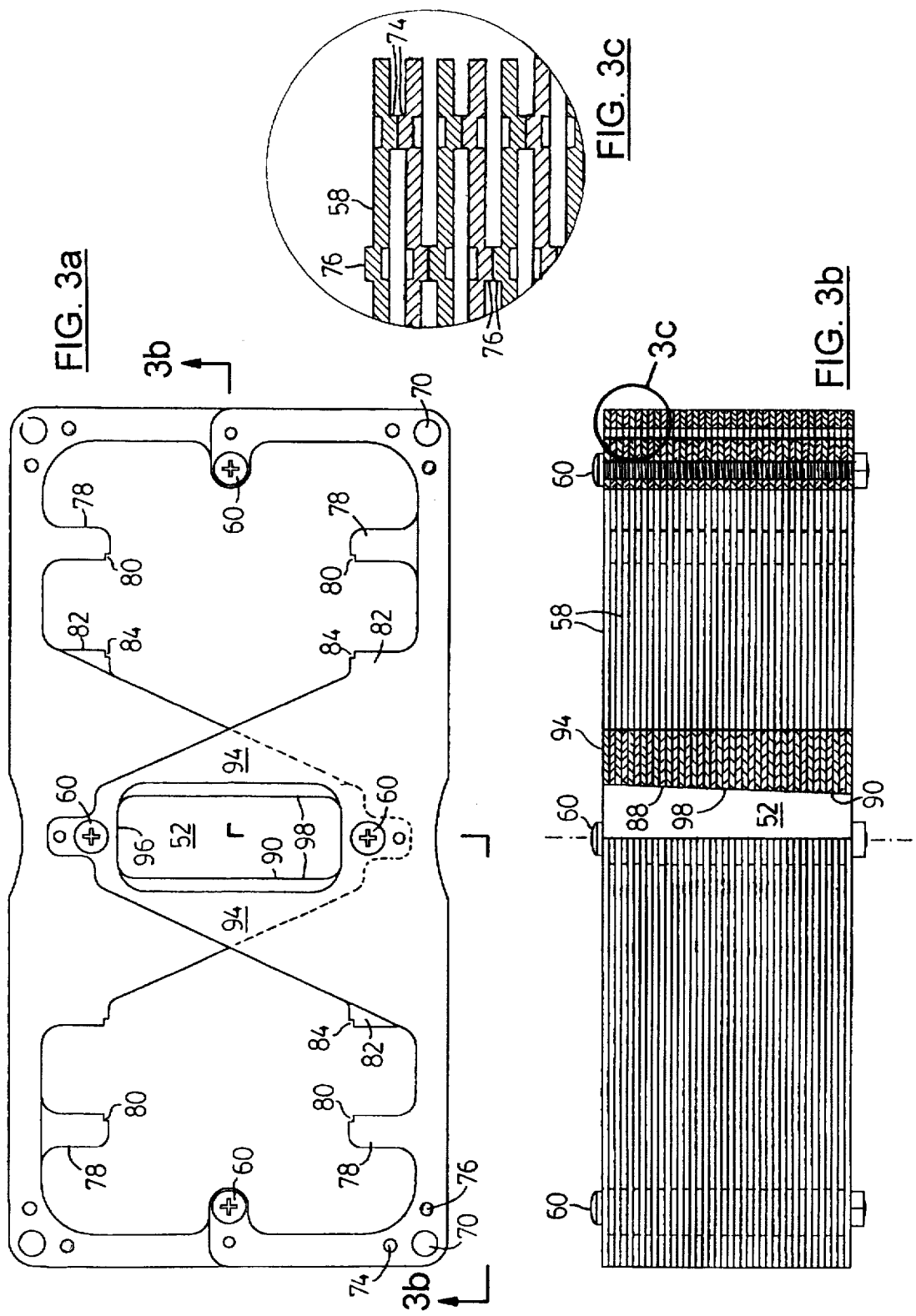

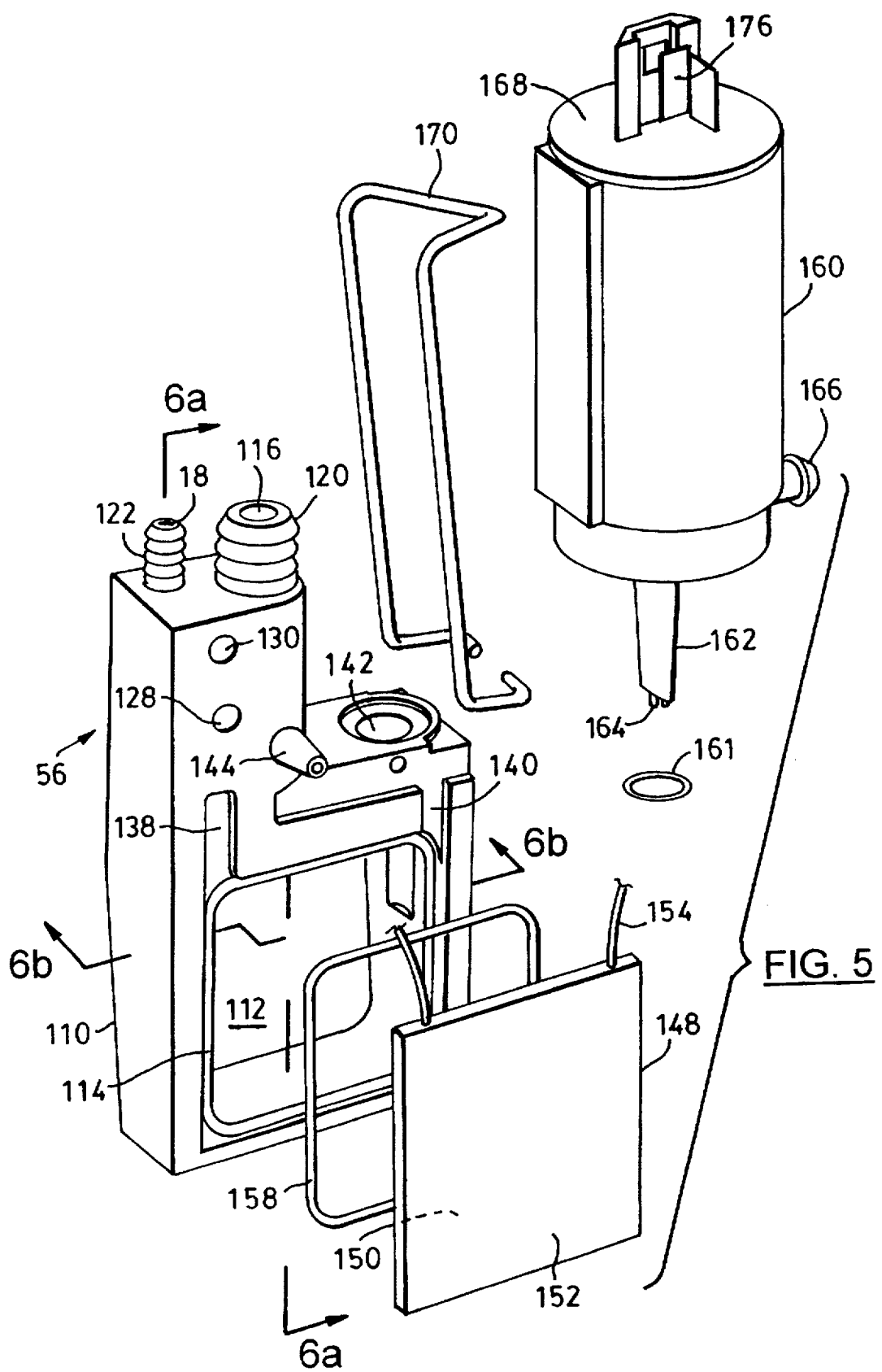

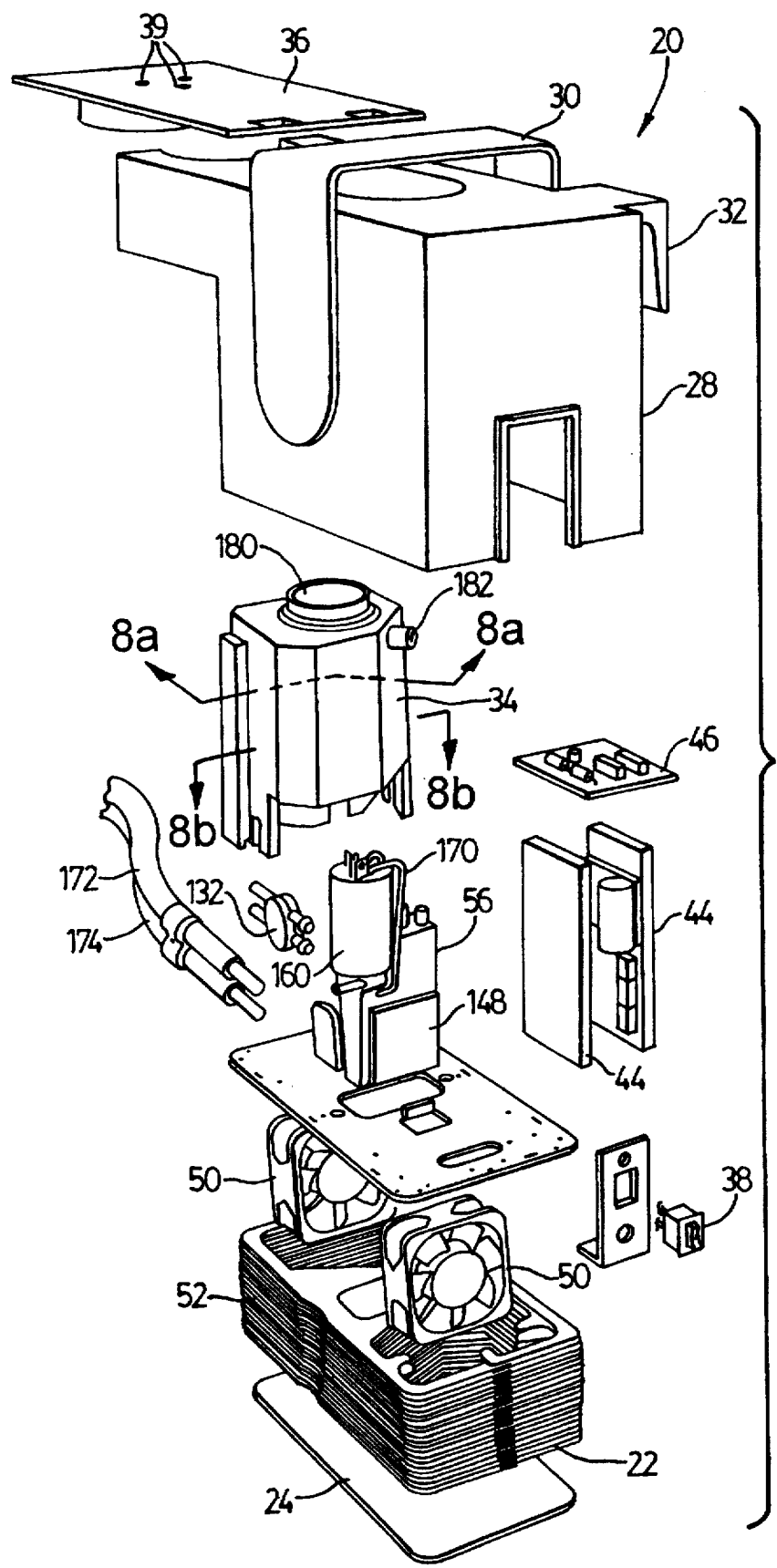

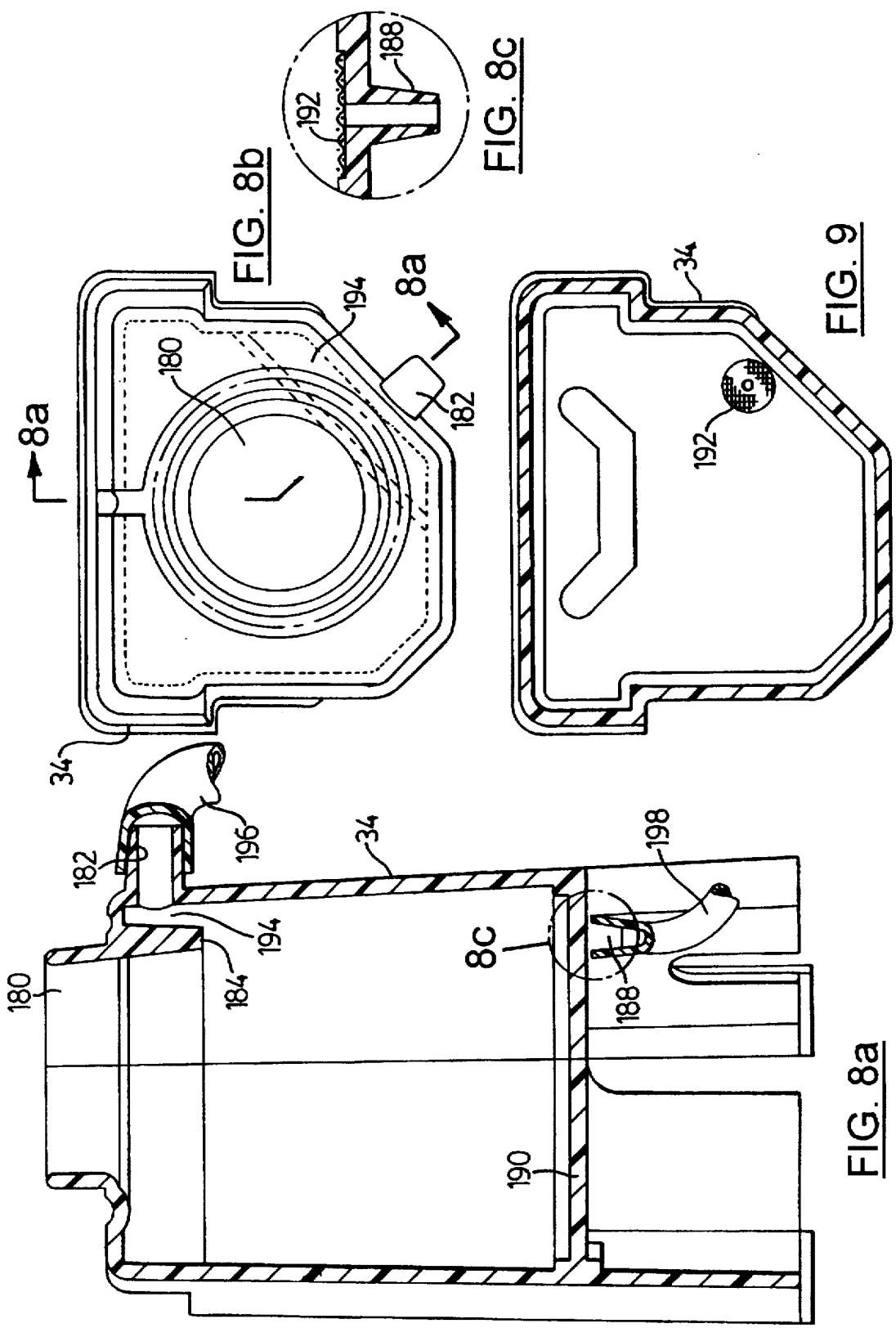

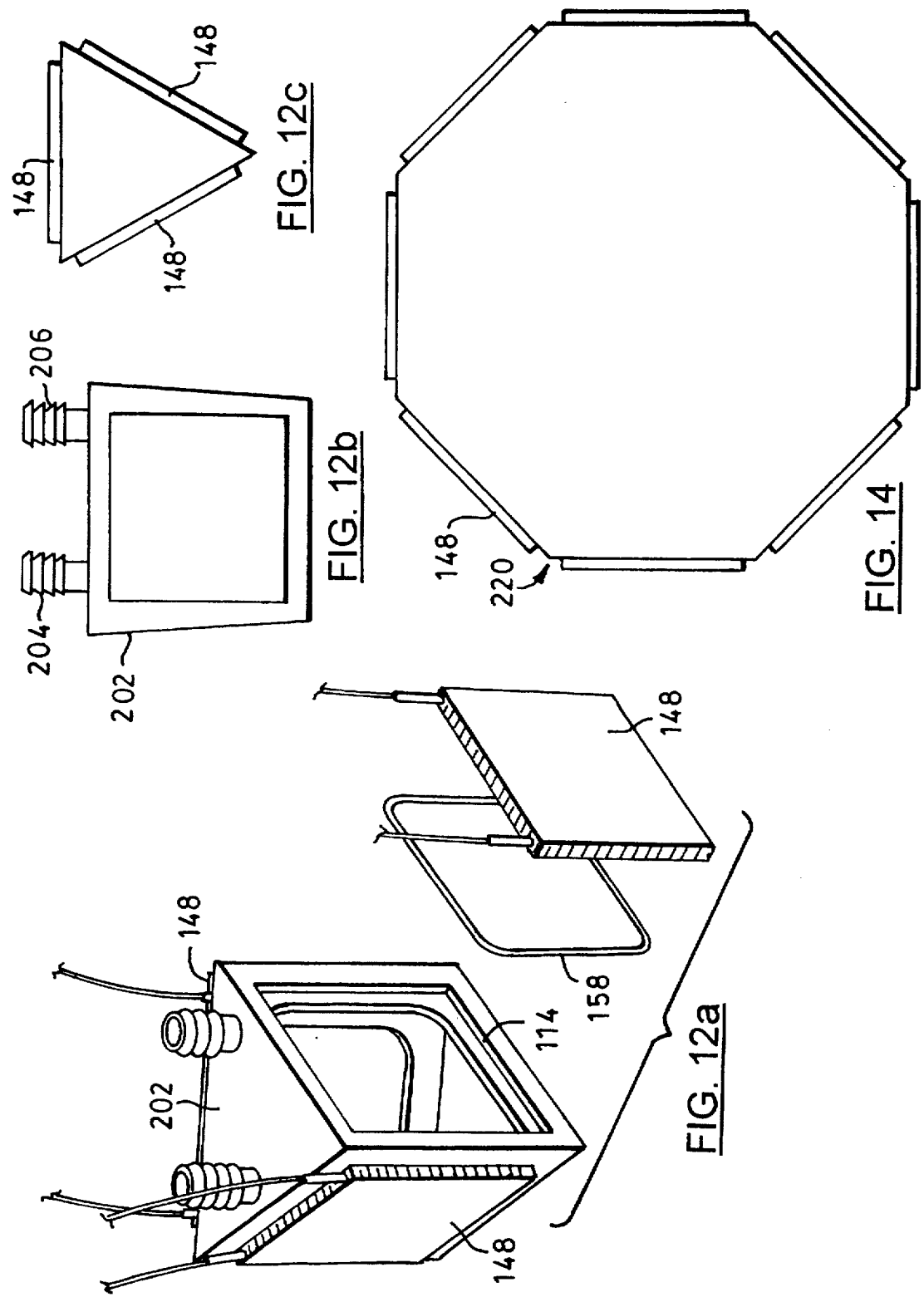

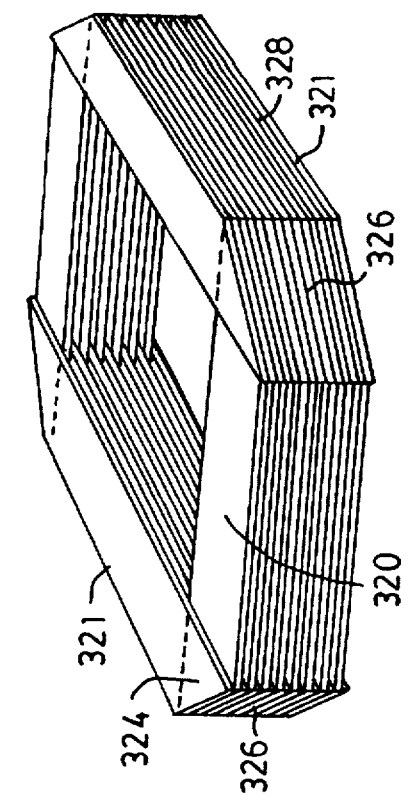
FIG. 15
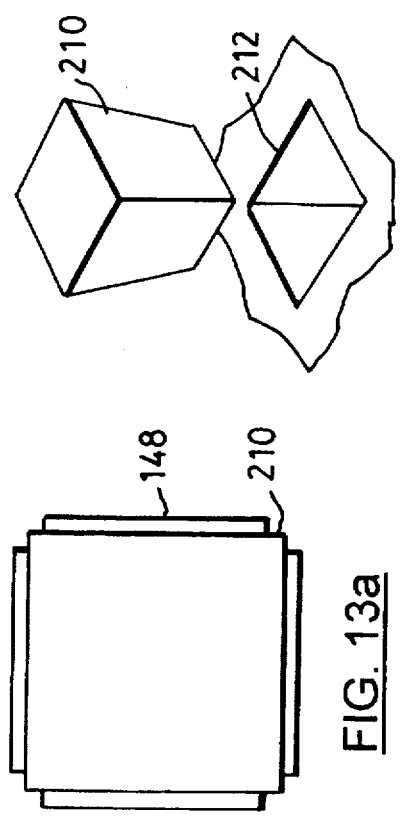
FIG. 13a
FIG. 13b
FIG. 16
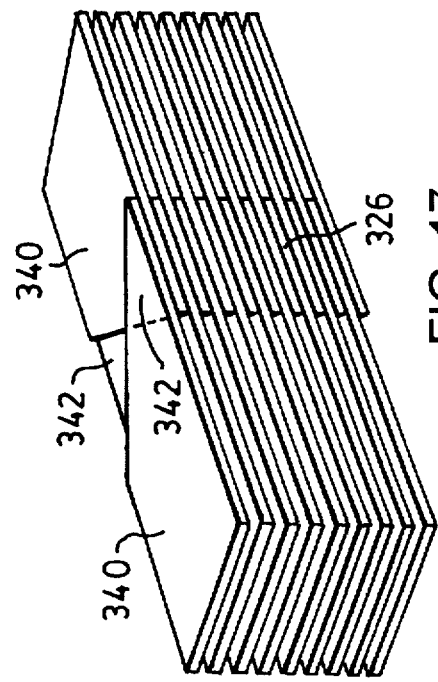
FIG. 17
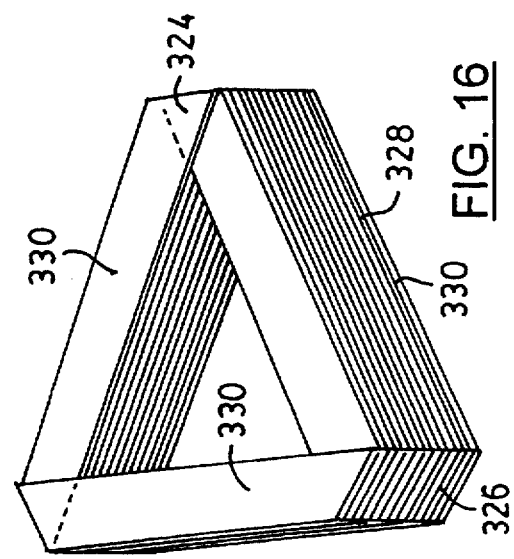

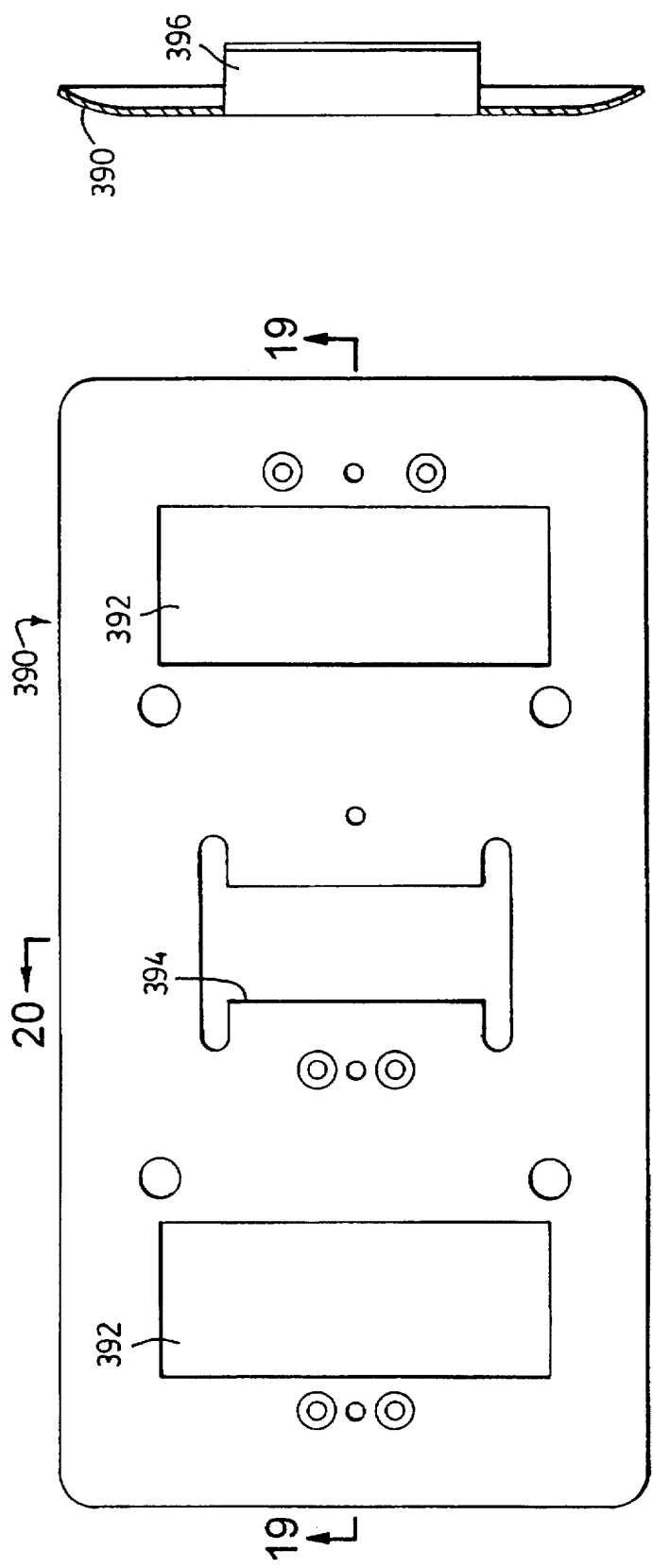
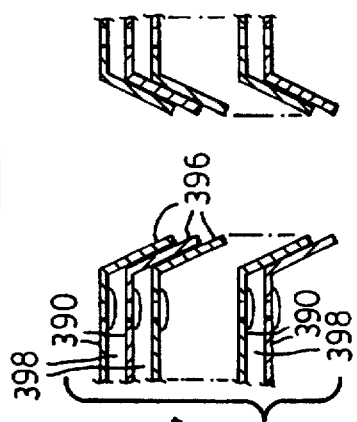
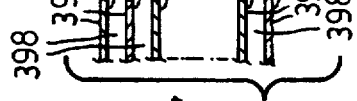
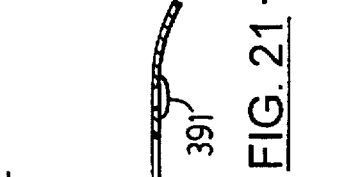

5,895,418

DEVICE FOR PRODUCING COLD THERAPY

CROSS REFERENCE TO RELATED APPLICATIONS

This patent application is a continuation-in-part application of U.S. patent application Ser. No. 08/316,352 filed on Sep. 30, 1994, entitled METHOD AND DEVICES FOR PRODUCING SOMATOSENSORY STIMULATION USING TEMPERATURE, now U.S. Pat. No. 5,628,769. This application also relates to United States Provisional patent application, Ser. No. 60/014,451, filed on Apr. 1, 1996, entitled DEVICES FOR PRODUCING SOMATOSENSORY STIMULATION USING TEMPERATURE.

FIELD OF THE INVENTION

The present invention relates to devices for cold and/or hot therapy and devices for cooling and/or heating adjacent areas on a person for therapeutic purposes.

BACKGROUND OF THE INVENTION

Pain abatement research is a major area of study which goes hand-in-hand with pain research itself. In many cases pain is a symptom of an underlying malady or trauma so the presence and nature of the pain in these cases is sometimes essential in aiding awareness and the diagnosis of the underlying illness. The abatement of pain has traditionally been effected using various external and internal treatments. Examples of external treatment include acupuncture, electro-shock treatment using transcutaneous electrical nerve stimulation (TENS), use of temperature such as application of hot or cold packs or topical application of cooling or heating formulations. Examples of internal, invasive treatments include drug treatments by oral administration or injection of freezing agents. Where feasible, the external physical methods of alleviating pain are preferable over the invasive, internal techniques for obvious reasons.

The application of hot or cold to localized pain such as muscle or tendon pain to reduce swelling has a long history. There are many devices for heating or cooling parts of the body. Hot water bottles and ice or cold packs are among the oldest and simplest devices for applying heat and cooling respectively. Another type of device is the heating blanket that uses electrical resistive heaters for heating. U.S. Pat. No. 4,094,357 discloses a heat transfer blanket which uses heat pipes coupled to heating/cooling systems. U.S. Pat. No. 5,269,369 teaches a body suit which utilizes a system of heat pipes to redistribute body heat for heating or cooling the person wearing the suit.

U.S. Pat. No. 4,459,468 issued to Bailey discloses a temperature control fluid circulating system provided with a thermal blanket and a large refrigerant reservoir using thermoelectric units inserted directly into the reservoir to heat and cool the refrigerant in the reservoir. U.S. Pat. No. 3,154,926 issued to Hirschhorn teaches a cooling blanket with a coolant reservoir with substantially all of one side of the reservoir in contact with thermoelectric Peltier units to cool the liquid in the reservoir. U.S. Pat. No. 4,523,594 issued to Kuznetz discloses a heat exchange jacket that can be used in an open loop mode or a closed loop mode. In the open loop mode the jacket is connected to a hot or cold water faucet in a hospital or home while in the closed loop mode a thermoelectric device is used to heat/cool water in the reservoir which is in series with a pump. Similarly, U.S. Pat. No. 3,967,627 issued to Brown is directed to a hot/cold applicator system utilizing a peristaltic pump in series with a patient blanket, a fluid reservoir and a heat exchanger for heating/cooling the fluid. A drawback to these types of devices is poor efficiency of cooling the refrigerant since essentially the entire volume of coolant contained in the reservoir must be cooled.

U.S. Pat. Nos. 4,962,761 to Golden and 5,174,285 to Fontenot disclose fluid circulation systems for use with thermal bandages, pads or blankets. These devices provide a thermal blanket with closed loop fluid circulation systems with fluid module housings which are in thermal contact with heating/cooling devices. A drawback to these types of devices is poor cooling efficiency for cooling the refrigerant since the latter contacts the cooling devices indirectly through the walls of the fluid modules.

U.S. Pat. No. 3,888,259 issued to Miley discloses hypothermia device for therapeutic applications. The device includes a fluid pump located between a heat exchanger and a reservoir and a double impeller pump with an upper impeller connected in series with the reservoir and the hot side of a thermoelectric unit and a lower impeller pump connected in series with the cold side of the thermoelectric unit and the patient blanket. Once water fills the system during operation of the pumps a quasi closed-loop is set up for the cooling water circulated between the blanket, the second set of impellers and the cooled side of the thermoelectric unit. A drawback to this system is the need for two pumps to sustain the pumping action in the two circulation systems.

U.S. Pat. No. 4,170,998 to Sauder is directed to a portable cooling apparatus for cooling a limb of a patient which includes a compressor and evaporator for condensing and evaporating the refrigerant. A drawback to this type of system and others like it is that they are quite bulky and awkward since they use large fluid pumps between the heat exchanger and the blanket or pad being heated or cooled. Some of the systems employ condensers, refrigerants and evaporator coils which are also bulky, awkward and of limited mobility.

It would therefore be advantageous to provide compact and economical devices for thermal treatment of maladies or trauma of the body provided with an efficient method of rapidly cooling/heating the refrigerant.

SUMMARY OF THE INVENTION

It is an object of the present invention to provide a compact and portable heat exchange device for heat exchange therapy of patients.

In one aspect the present invention provides a portable heat exchange device for heat exchange therapy of a patient. The device comprises a heat exchange pad means having at least one fluid inlet and one fluid outlet through which a fluid exchange medium may be circulated through the pad means. The device includes a heat exchange module including a first housing having a fluid recirculation inlet and a fluid recirculation outlet and conduit means communicating the recirculating fluid inlet and the recirculating fluid with the fluid outlet and fluid inlet, respectively, of the pad means. A first chamber is located within the first housing in fluid communication with a source of fluid heat exchange medium and the fluid recirculation inlet and fluid recirculation outlet. The first housing has at least one opening into the first chamber, and one of either a heat source and a heat sink having an inner surface is mounted within the opening with the inner surface in heat exchange relationship with the fluid heat exchange medium within the first chamber. The device includes means for circulating the fluid heat exchange medium through the first chamber so as to contact the inner surface and to convey the fluid heat exchange medium to the recirculating fluid outlet to the pad means.

In a preferred embodiment, the one of either a heat source and heat sink is a thermoelectric Peltier unit comprising the inner surface and having an opposed outer surface.

In another aspect of the invention there is provided a portable therapeutic heat exchange device comprising heat exchange pad means having at least one fluid inlet and one fluid outlet through which a fluid heat exchange medium may be circulated through the pad means. The heat exchange device includes a heat exchange module including a housing provided with a fluid recirculation inlet and a fluid recirculation outlet and conduit means communicating the recirculating fluid inlet and the recirculating fluid outlet with the fluid outlet and fluid inlet respectively, of the heat exchange pad means. The housing includes a chamber in flow communication with a source of fluid heat exchange medium and the fluid recirculation inlet and the fluid recirculation outlet. The housing includes at least one opening that opens into the chamber and a thermoelectric Peltier unit having a heated outer surface and a cooled inner surface is mounted within the opening with the inner surface in heat exchange relationship with the fluid heat exchange medium within the chamber. The device includes means for circulating the fluid heat exchange medium through the chamber so as to contact the cooled inner surface and to convey the fluid heat exchange medium to the recirculating fluid outlet to the pad means. The device includes a heat exchanger with a heat exchanger chamber, a thermally conducting solid portion adjacent to the chamber and a finned portion extending from the solid portion. The cooling module is seated in the heat exchanger chamber with the outer heated surface thermally contacted to the solid portion.

In another aspect of the invention there is provided a compact heat exchange device for cooling and/or heating a heat exchange fluid. The device comprises a heat exchange module including a first housing having a fluid recirculation inlet and a fluid recirculation outlet, a first chamber within the first housing in fluid communication with the fluid recirculation inlet and the fluid recirculation outlet. The first housing is provided with at least one opening in the into the first chamber and a thermoelectric Peltier unit having a first surface and an opposed second surface is mounted within the at least one opening and is in liquid tight sealing relationship with the housing with the first surface in heat exchange relationship with a fluid heat exchange medium within the first chamber. The device includes a first pump with a first impeller, the first pump being attached to the first housing in communication with the fluid recirculation outlet to pump for circulating the heat exchange fluid through the first chamber so as to contact the first surface and to convey the heat exchange fluid through the recirculating fluid outlet.

The present invention also provides heat exchanger comprising a thermally conducting solid portion having a heat exchanger chamber with at least one surface adapted to receive thereagainst and object to be cooled. The heat exchanger includes a thermally conducting finned portion in thermal contact with the thermally conducting solid portion. In a preferred embodiment of the heat exchanger, the heat exchanger comprises a plurality of heat exchange plates assembled in a stacked relationship wherein each heat exchanger plate has a central section and at least one fin portion extending from the central section. The central section of each heat exchanger plate has an aperture and the central sections of adjacent heat exchange plates are partially overlapped to form the thermally conducting solid portion with the apertures in registration to define walls of the heat exchanger chamber. The fin portions of adjacent plates in the stack are spaced by dimples located on each fin portion of the plate.

BRIEF DESCRIPTION OF THE DRAWINGS

The following is a description, by way of example only, of heat exchange therapy devices constructed in accordance with the present invention, reference being had to the accompanying drawings, in which:

FIG. 1 is a perspective view of an apparatus for heating and cooling constructed in accordance with the present invention;

FIG. 2 is a cross sectional view along line 2—2 of FIG. 1;

FIG. 3a is a top view of a heat exchanger forming part of the apparatus in FIG. 1;

FIG. 3b is a sectional view along the line 3b—3b of FIG. 3a;

FIG. 3c is an enlarged view of the circled portion of FIG. 3b;

FIG. 5 is an assembly view of a cooling module forming part of the present invention;

FIG. 7a is an exploded perspective view of the apparatus of FIG. 1;

FIG. 8a is a sectional view along line 8a—8a of FIG. 8b;

FIG. 8b is a top view of the water reservoir of FIG. 7a;

FIG. 8c is an enlarged sectional view of the circled portion of FIG. 8a;

FIG. 9 is a sectional view along the line 9—9 of FIG. 7b;

FIG. 12a is a perspective view of an alternative embodiment of a cooling chamber according to the present invention;

FIG. 12b is an elevational view of the cooling chamber of FIG. 12a;

FIG. 12c is a bottom view of the cooling chamber of FIG. 12a;

FIG. 13a is a bottom view of an alternative embodiment of a cooling unit according to the present invention;

FIG. 13b is a perspective view of the cooling unit of FIG. 13a and associated heat exchanger, having a portion removed;

FIG. 14 is a bottom view of an alternative embodiment of a cooling unit according to the present invention;

FIG. 15 is a perspective view of an alternative embodiment of a heat exchanger of the present cooling device;

FIG. 16 is a perspective view of another embodiment of a heat exchanger of the present cooling device;

FIG. 17 is a perspective view of another alternative embodiment of a heat exchanger of the present cooling device;

FIG. 18 is a top view of another alternative embodiment of a heat exchanger of the present cooling device;

FIG. 19 is a cross sectional view along the line 19—19 of FIG. 18;

FIG. 20 is a cross sectional view along the line 20—20 of FIG. 18;

FIG. 21 is a sectional view, broken away, showing several plates in FIG. 19 stacked to form a cooling chamber;

FIG. 26b is an exploded view of the section of FIG. 26a;

DETAILED DESCRIPTION OF THE INVENTION

Figure 4:
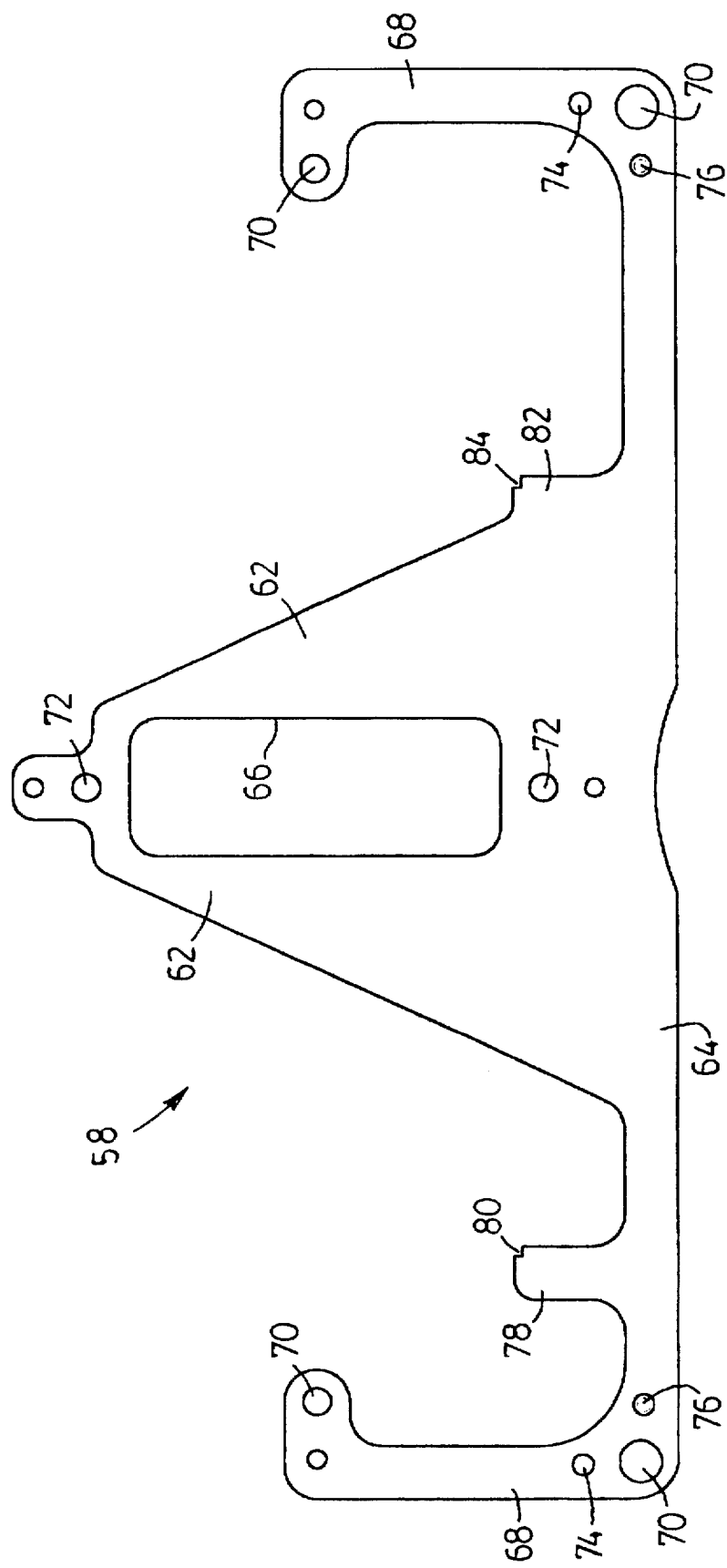
FIG. 4 is a top view of the structural member from which the heat exchanger of FIG. 3a is constructed.

FIGS. 1 and 2 show a cooling apparatus 20 constructed in accordance with the present invention. Cooling apparatus 20 includes a heat exchanger 22 with a base plate 24 and four grommets 26 attached to base plate 24 to provide a support for the device. A housing 28 is mounted on top of heat exchanger 22 and is provided with a carrying handle 30 for carrying the assembled apparatus. Housing 28 includes a pair of spaced hooks 32, best seen in FIG. 1, disposed along one side of housing 28 for hooking the apparatus 20 onto a bed railing or wall rail beside a patient using the device. An on-off switch 38 and a cord 40 provide power to the apparatus.

Referring specifically to FIG. 2, housing 28 encloses two power supplies 44 and a control circuit 46 mounted on top of the power supplies. Housing 28 encloses a reservoir 34 having a pop-top lid 36 for filling the reservoir. Heat exchanger 22 contains two cooling fans 50 one located on each side of a cooling chamber 52. Cooling module 56 is received into cooling chamber 52.

Referring to FIGS. 3a to 3c and FIG. 4, heat exchanger 22 is constructed by overlapping alternating heat conducting plates 58, preferably aluminum, where all the elements are structurally identical. Four bolts 60 are used to secure the stack of elements 58 together. Referring to FIG. 4, each heat conducting element 58 is has a triangular middle section 62 having a base 64 and elongate L-shaped frame members 68 extending from base 64. The middle section 62 encloses a rectangular aperture 66. Element 58 includes holes 70 at both ends of arms 68 in addition to holes 72 in the middle portion 62 through which bolts 60 are inserted to secure the assembled heat exchanger together. The end portions 68 are provided with dimples 74 extending upwardly out of the plane of plate 58 and dimples 76 extending downwardly in the opposite direction. A tab 78 extends outwardly from arm 68 and is provided with a notch 80. One of the triangular sections 62 is provided with a triangular protrusion having a notched apex 84.

The stack of plates 58 is assembled as shown in FIG. 3b so the dimples 74 and 76 line up as seen in the enlargement of FIG. 3c. The chamber 52 (FIG. 3a) thereby formed is originally rectangular because all the apertures 66 (FIG. 4) are the same size. The tapered chamber 52 in FIG. 3b is obtained by machining out the heat exchanger chamber so that the upper portion 88 of the chamber 52 is wider and tapers to the lower portion 90. The inner walls of 96 and 98 of tapered chamber 52 are essentially solid since the plates 58 are tightly compressed together before machining. The triangular portions 94 formed by the overlapping sections 62 of each plate 58 in the assembled heat exchanger form a thermally conducting solid portion and the elongate frame members 68 extending out from the solid portion form the finned portion of the exchanger with a gap between adjacent plates in the finned section due to dimples 74 and 76 acting as spacers.

Referring to FIG. 3a, when heat exchanger 22 is assembled from plates 58, notches 84 and 80 on each side of chamber 52 define a rectangular volume. The cooling fans 50 (FIG. 2) fit into these rectangular volumes. The solid triangular portions 94 provide excellent heat conduction away from walls 98 into the finned portion of the heat exchanger. The heat flow from chamber wall 98 into the finned portion of the heat exchanger is parallel to the surface of the plates thereby advantageously providing optimum heat transfer from wall 98 to the surface area for heat dissipation. The size of the solid portion of the heat exchanger is preferably kept to a minimum as it is required to conduct heat from the thermal contact surfaces to the finned portions.

Figure 6B:
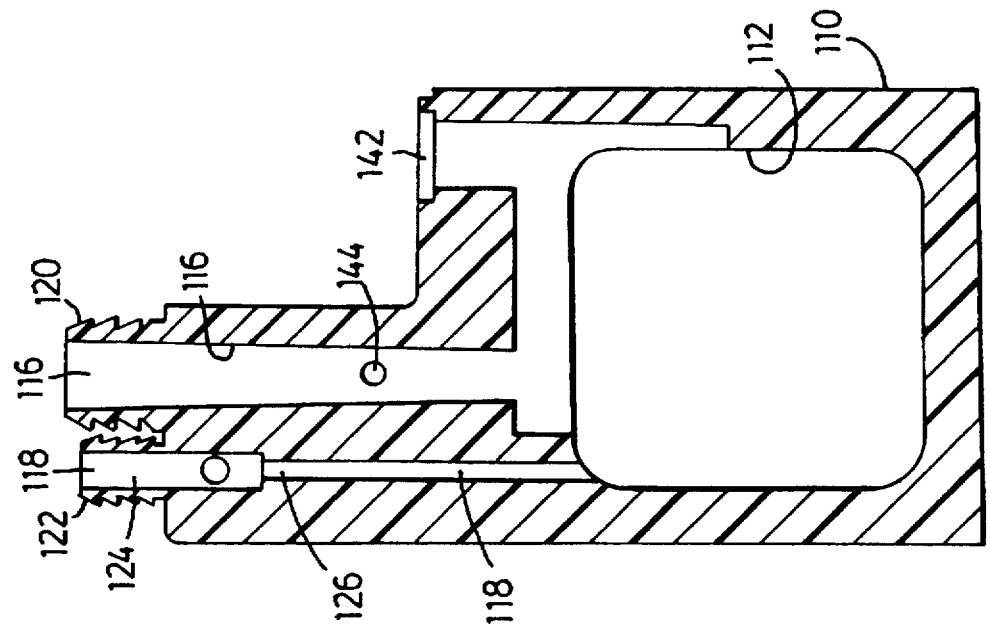
FIG. 6b is a sectional view along line 6b—6b of FIG. 5.
Figure 6A:
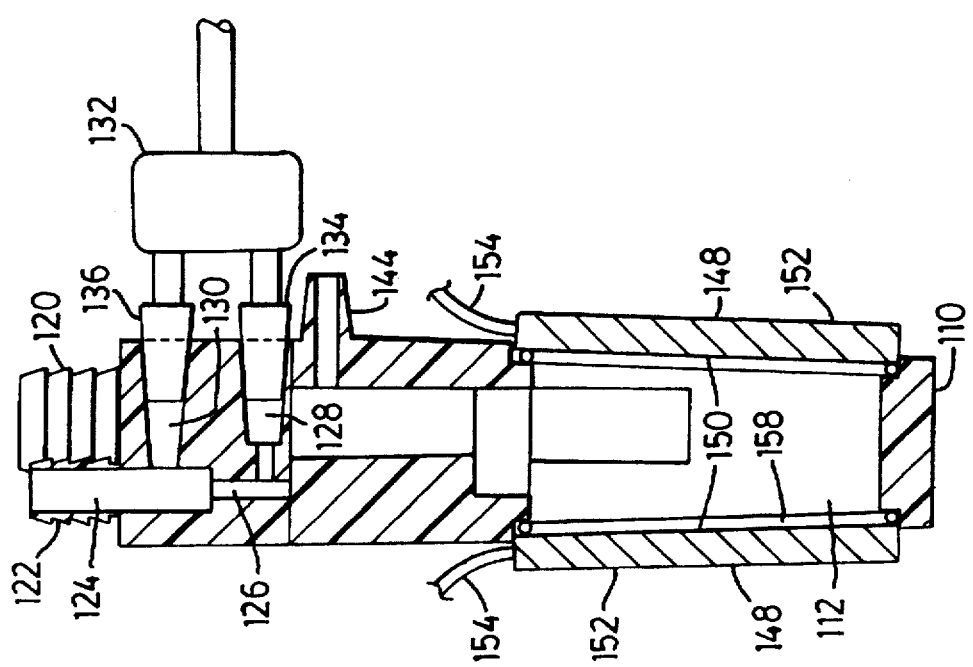
FIG. 6a is a sectional view along line 6a—6a of FIG. 5.

Details of cooling module 56 are shown in FIGS. 5, 6a and 6b. Cooling module 56 comprises a housing 110 that is tapered, best seen in FIG. 6a. The taper of housing 110 substantially matches the angle of the taper of chamber 52 in heat exchanger 22, see FIG. 3b. Housing 110 encloses a chamber 112 with opposed open sides with an O-ring groove 114 extending around the opening on each face. As shown in FIGS. 5 and 6b, housing 110 includes passageways 116 and 118 into which spigots 120 and 122 respectively are inserted. Alternatively, spigots 120 and 122 may be formed with housing 110 as a unitary structure as shown in FIG. 6b. Referring specifically to FIG. 6b, passageway 118 is the fluid flow path back into chamber 112 from the cooled blanket and includes an upper wider channel 124 and a narrower lower channel 126 in flow communication with chamber 112. A channel 130 extends through housing 110 to communicate with upper channel portion 124 and a channel 128 extends through the housing to communicate with lower channel portion 126, best seen in FIG. 6a.

Cooling module 56 is provided with a liquid pressure/flow sensor 132 having spaced conduits 134 and 136 inserted into passageways 128 and 130 respectively. Pressure/flow sensor 132 is placed in the flow circuit with the restriction between passageways 124 and 126 located between its inputs. The restriction creates a pressure difference across sensor 132 which indicates flow and no flow conditions. Silicon pressure sensors, model numbers MPX10, MPX11 and MPX12 produced by Motorola have been found to be quite adequate.

Housing 110 is provided with a channel 142 in flow communication with chamber 112. A fitting 144 protruding from housing 110 is in flow communication with passageway 116 and is used for filling chamber 112 when the cooling module is assembled. Passageway 116 provides an air return line from chamber 112 to reservoir 34 so that air is displaced from chamber 112 into reservoir 34 as the chamber is being filled.

Referring to FIGS. 5 and 6a, the openings in the two opposing faces of housing 110 are rectangular and are adapted to receive thermoelectric units 148 with the edges of the units sealing against the O-ring 158 seated in O-ring groove 114 to form a tight seal. Each thermoelectric unit 148 includes opposed surfaces 150 and 152 and a pair of wires 154 which are electrically connected to the control circuit 46 (FIG. 7a). A pair of groves 138 and 140 extend upwardly from O-ring groove 114 and provide a channel for each of the electrical wires 154. A liquid pump 160 is coupled to housing 110 with an O-ring seal 161 and spring bracket 170 and the pump comprises a impeller shaft housing 162 in which an impeller 164 is housed. The impeller housing 162 is inserted into passageway 142 and the pump is secured to the housing by means of the spring bracket 170 which is pivotally attached to the housing 110 and snaps over the upper end 168 of the pump. When pump motor 160 is coupled to housing 110 a portion of the impeller housing 162 and impeller 164 are located in chamber 112 adjacent to the inner cooled surface 150 of thermoelectric module 148 to ensure a vigorous flow of fluid against the module surfaces. Electrical connection is made to pump 160 through the plug 176 protruding from end portion 168. Pump 160 is provided with a liquid outlet 166 for circulating the cooled liquid out of chamber 112.

Referring to FIGS. 8a, 8b and 9, water reservoir 34 is preferably moulded of a translucent plastic to allow viewing of the water or liquid level in the reservoir but which does not become unsightly as would a clear plastic after prolonged exposure to tap water. Reservoir 34 has an opening 180 for filling with water or other heat exchange fluid. An air return line connection 182 is located at the top of the reservoir and an air line 196 is attached thereto at one end. The reservoir 34 is provided with a downwardly extending section 184 spaced away from the outer wall containing the air return line connection 182 thereby defining a gap 194. The air return line is protected from the reservoir being overfilled by an air pocket forming in gap 194 thus preventing water from filling the air return. A filler spigot 188 is located on the bottom 190 of the reservoir and a filter 192 covers the outlet passageway, best seen in FIG. 9. A filler tube 198 is attached to spigot 188 at one end thereof. Reservoir lid 36 is provided with several small holes 39 (FIG. 7a) which are small enough to resist water flow due to surface tension but large enough to allow easy passage of air. Lid holes 39 advantageously permit the chamber 112 to be filled with fluid from reservoir 34 without creating a vacuum. The volume of fluid into chamber 112 is replaced with a volume of air through holes 39.

Figure 7B:
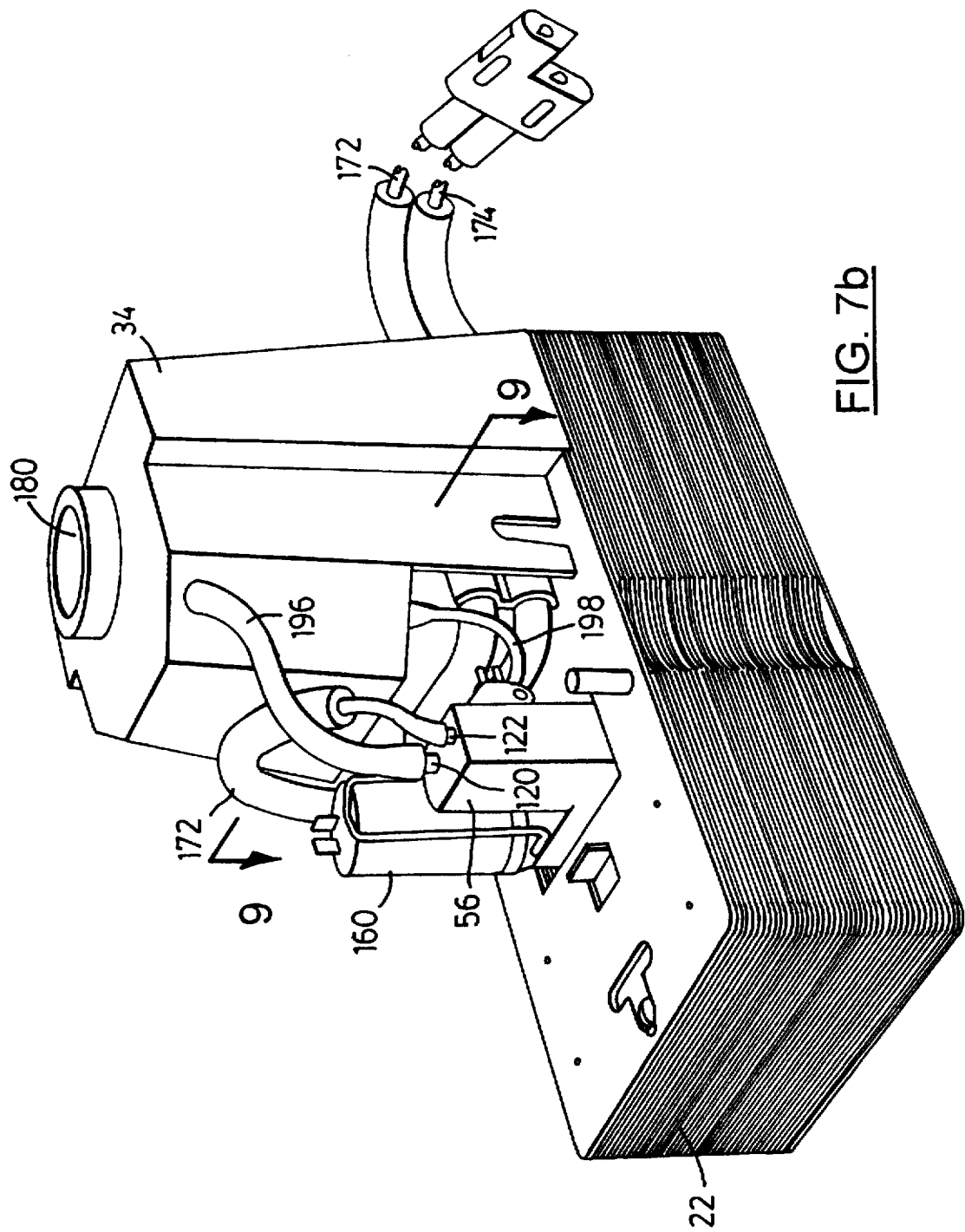
FIG. 7b is a perspective view of the cold therapy device of FIG. 1 partially assembled.
Figure 10:
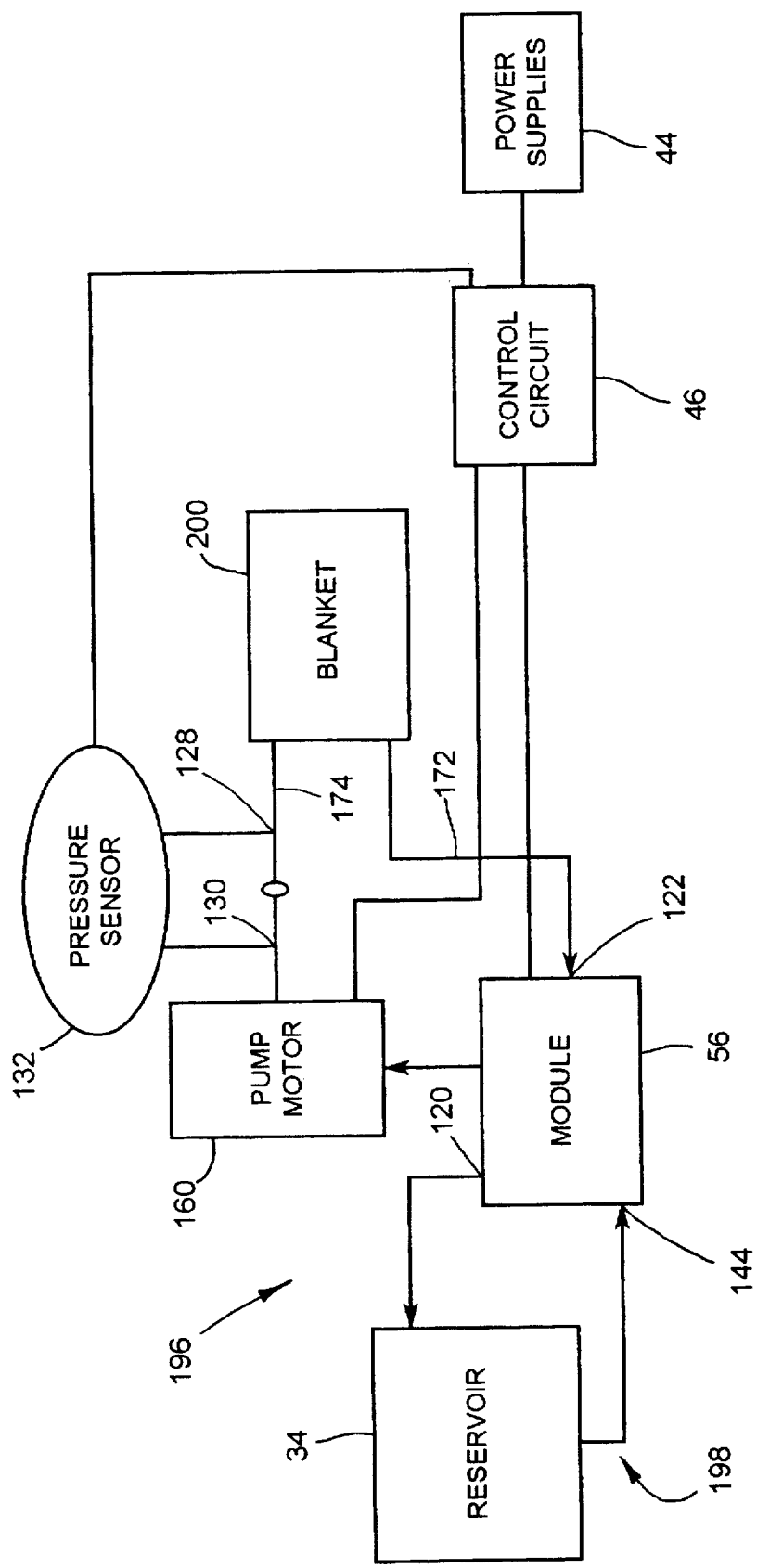
FIG. 10 is a diagrammatic illustration of the cold therapy device of FIG. 1.

With reference to FIG. 7b, tube 198 is attached to spigot 144 (FIG. 5) located on the housing of cooling module 56 to provide a cooling liquid supply to the cooling unit from reservoir 34. The other end of air line 196 is connected to air return spigot 120. Hose 172 is connected to spigot 122 and provides the liquid return line from the cooling blanket. Hose 174 is connected at one end to fitting 166 on pump 160 and the other end is connected to the cooling blanket thereby supplying liquid to the blanket 200 (FIG. 10).

In operation, heat is extracted out of the fluid in chamber 112 by the two thermoelectric units 148 (FIGS. 6a and 7a). Specifically, thermoelectric units 148 transfer the heat to heat exchanger 22 which dissipates the extracted heat into the air. The two fans 50 are inserted in the heat sink 22 and force air over the surface of the fins 58 and facilitates the dissipation of the heat into the air. Referring to the diagrammatic representation in FIG. 10, the cold fluid from chamber 112 is circulated through a patient wrap 200 which is placed directly on the area of the patient to be treated. The cold fluid is drawn up from the cooling chamber 112 by pump 160 and delivered to the wrap or cooling blanket 200 through tube 174. The water returns from the blanket 200 to housing chamber 112 in cooling module 56 through the return tube return line 172. Water reservoir 34 is provided with a reserve of fluid which ensures a full flow circuit to maximize performance and prevent damage to the apparatus. Chamber 112 in the cooling module housing 110 has a volume substantially smaller than the fluid containing volume within reservoir 34. The refrigerant is not circulated directly through reservoir 34 as in many of the prior art devices but rather the reservoir is in flow communication with cooling module 56 so that the reservoir acts as sink or source for when a condition of an excess or deficit respectfully of refrigerant circulated through the patient blanket exists. This is best seen in the block diagram of FIG. 10. This feature, in addition to the fact that the refrigerant in the reservoir is not cooled and the feature of the cooling module and pump assembly having a configuration to ensure a vigorous flow of refrigerant directly over the cooled surface gives a significantly improved cooling efficiency over the prior art devices.

Figure 11:
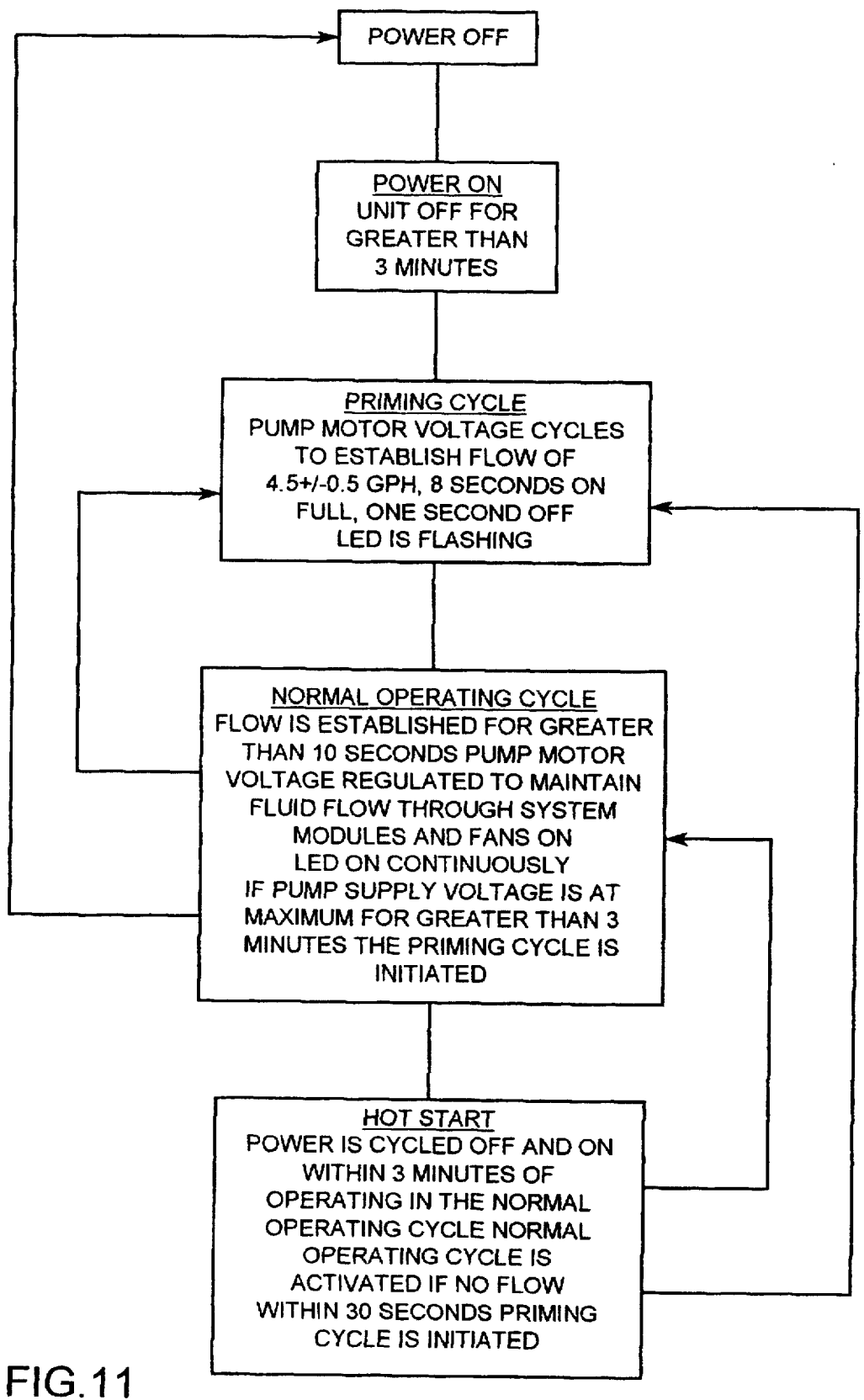
FIG. 11 is a flow diagram of the operating logic employed in the control circuit forming part of the cooling apparatus.

Power to cooling apparatus 20 in FIG. 1a is controlled by on/off switch 38. When activated the device runs at maximum cooling. There are no user/operator adjustments on the units. The two power supplies 44 provide power to the control circuit and the control circuit in turn controls the thermoelectric modules 148, fans 50 and pump 160. The system is designed to maximize pump-motor life and provide the preset flow rate conditions (4.0 to 4.5 gallons per hour). Referring again to the diagrammatic representation in FIG. 10, control circuit 46 achieves this by monitoring pressure/flow sensor 132 and regulating the supply voltage to pump 160 to maintain water flow between cooling module 56 and patient blanket 200 without exceeding the maximum voltage limitations. Should the voltage remain at the maximum for longer than 3.0 minutes a clearing cycle is initiated. The pump voltage is switched on for 8 seconds at 5.5 volts and off for 1 second. This cycle continues until the flow returns to normal operating levels. Details of the operating logic are shown in the flow diagram in FIG. 11.

The smooth, continuous opposing walls 98 of heat exchanger 22 conduct heat from the outer hot surfaces 152 of thermoelectric units 148 through the triangular shaped overlapping sections 94 and the heat is conducted into the fin sections having air gaps between adjacent fins to dissipate heat. Thus, heat exchanger 22 is provided with very efficient heat dissipation by designing the heat exchanger with similarly shaped plates which have an overlapping solid portion which very efficiently conducts heat from the thermoelectric units to the air cooled finned section. When tapered housing 110 with thermoelectric units 148 engaged against the open faces is inserted into chamber 52 with the thermoelectric units engaged against the O-rings in housing 110, the matching tapered shape of chamber 52 acts to lock the cooling assembly in place and provides a tight fit which ensures good thermal contact between the cooling module and the heat exchanger. The outer surface 152 of thermoelectric units 148 are preferably coated with thermal joint compound prior to being inserted into chamber 52 to ensure good heat transfer between thermoelectric units 148 and heat exchanger 22.

Those skilled in the art will appreciate that numerous alternative embodiments of the present cold therapy device may be constructed and still fall within the scope of the present invention.

FIGS. 12a to 12c illustrate a triangular cooling chamber housing 202 with three thermoelectric units 148 and water inlet 204 and outlet 206.

FIGS. 13a and 13b illustrate a four-sided cooling chamber 210 provided with four thermoelectric units 148. The corresponding heat exchanger 212 is provided with four sections similar to sections 94 in heat sink 22 in FIG. 3a to provide efficient heat transfer from cooling chamber 210 to the finned portion of the heat exchanger (not shown). FIG. 14 illustrates an eight-sided cooling chamber 220 provided with eight thermoelectric units 148. These embodiments of the cooling chamber are advantageous for increasing cooling capacity. The cooling units are tapered as are the corresponding heat exchanger chambers in the heat exchangers into which the units are inserted.

FIGS. 15 to 17 illustrate alternative embodiments of the heat exchanger which may be constructed according to the present invention. In FIG. 15, four plates 321 shaped as symmetric trapezoids are overlapped as shown and triangular-shaped corner portions 324 have a continuous outer wall 326 which can conduct heat to the finned section comprising alternating metal plate 321/air gaps 328 where the heat is dissipated. Four surfaces 326 may be used to dissipate heat from heat sources adjacent to each surface. FIG. 16 illustrates the same principle but using three plates 330 instead of four. The structure of FIG. 17 provides a heat transfer surface 326 produced by overlapping metal plates 340 to form two triangular shaped sections 342 comprising alternating plates in contact with each other.

FIGS. 18 to 21 illustrate another embodiment of a heat exchanger constructed in accordance with the present invention. In this embodiment, a single plate 390 is provided with cut-out sections 392 and 394. From FIG. 19 it can be seen that plate 390 includes an inclined lip 396 in the cut-out section 394 on opposed edges. Referring to FIG. 21, when a plurality of the plates are assembled together, adjacent lip portions overlap to provide good thermal and mechanical contact between the lips 396. Holes 392 define fan receptacles while lips 396 and cut-out portions 394 define a central cooling chamber into which a cooling module is inserted (not shown). As with the previously described cooling chambers, the geometry of lips 396 and the tapered module provides good heat transfer to the air gaps 398 located between adjacent plates spaced from lips 336. Lips 336 are machined to provide a smooth uniform tapered surface. Dimples 391 are located on the bottom side of plate 390 which act as spacers in the stack. In heat exchanger 390 the solid portion is defined by the narrow overlapped lips 396.

It will be understood that the substantial improvement in heat dissipation achieved with the heat exchangers disclosed herein is obtained by the combination of a solid surface (to which good thermal contact is made by the heat producing object) which extends into a finned heat dissipation area. The number of solid sections in any one heat exchanger may be tailored to accommodate any number of objects from which heat dissipation is desired. The configuration in FIG. 16 may be used to cool three objects, the arrangement in FIG. 15 may be used to cool four objects making thermal contact at positions 326. The preferred embodiments disclosed herein utilize aluminum plates provided with dimples extending transversely in both directions from the plane of the plate. Stacking the plates provides a solid central section with a finned section having air gaps between the plates except at the locations where the plates contact the dimples of the adjacent plates. However, it will be appreciated that a solid block could be machined to provide both a solid portion and the finned section as an alternative to use of multiple plates disclosed herein.

Figure 22:
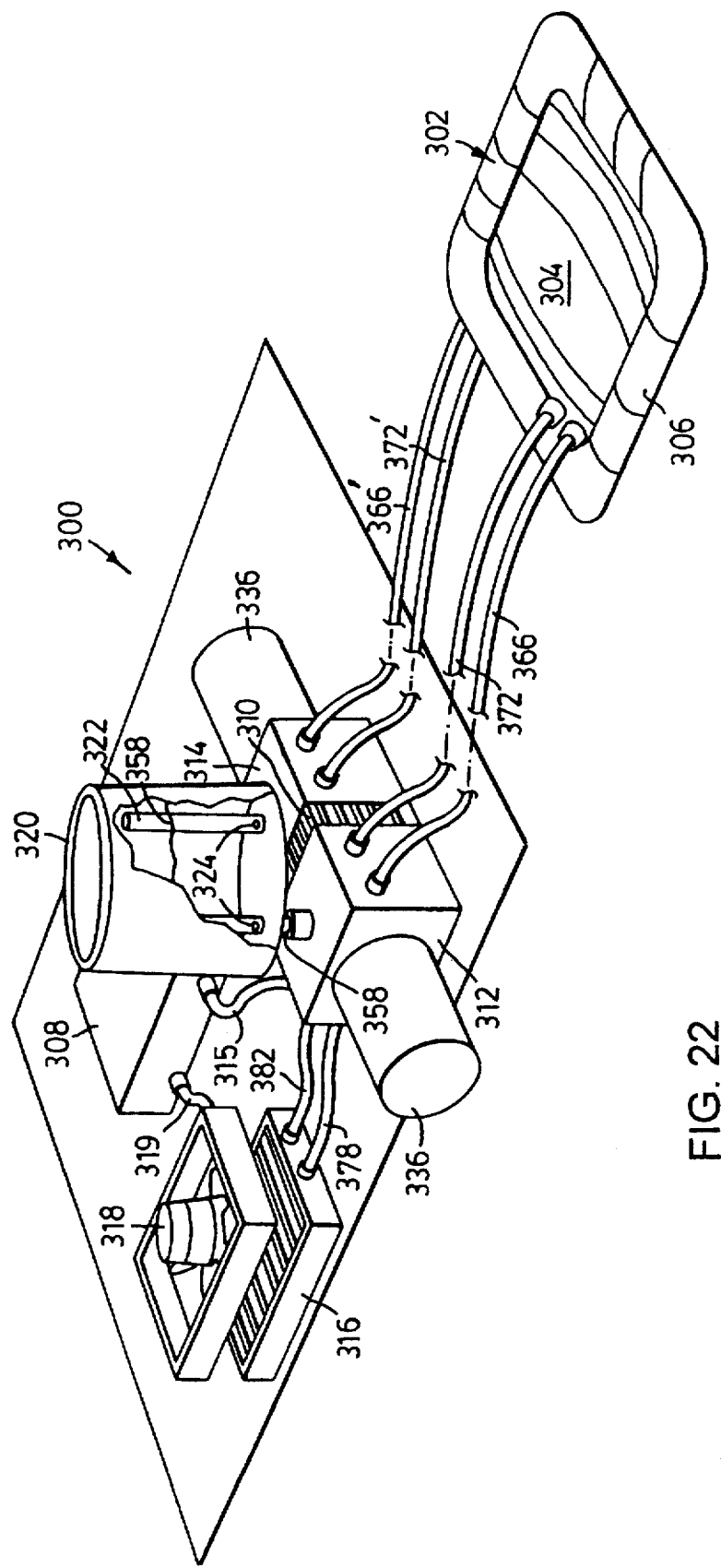
FIG. 22 is a perspective view of an alternative embodiment of an apparatus for heating and cooling constructed in accordance with the present invention.
Figure 23:
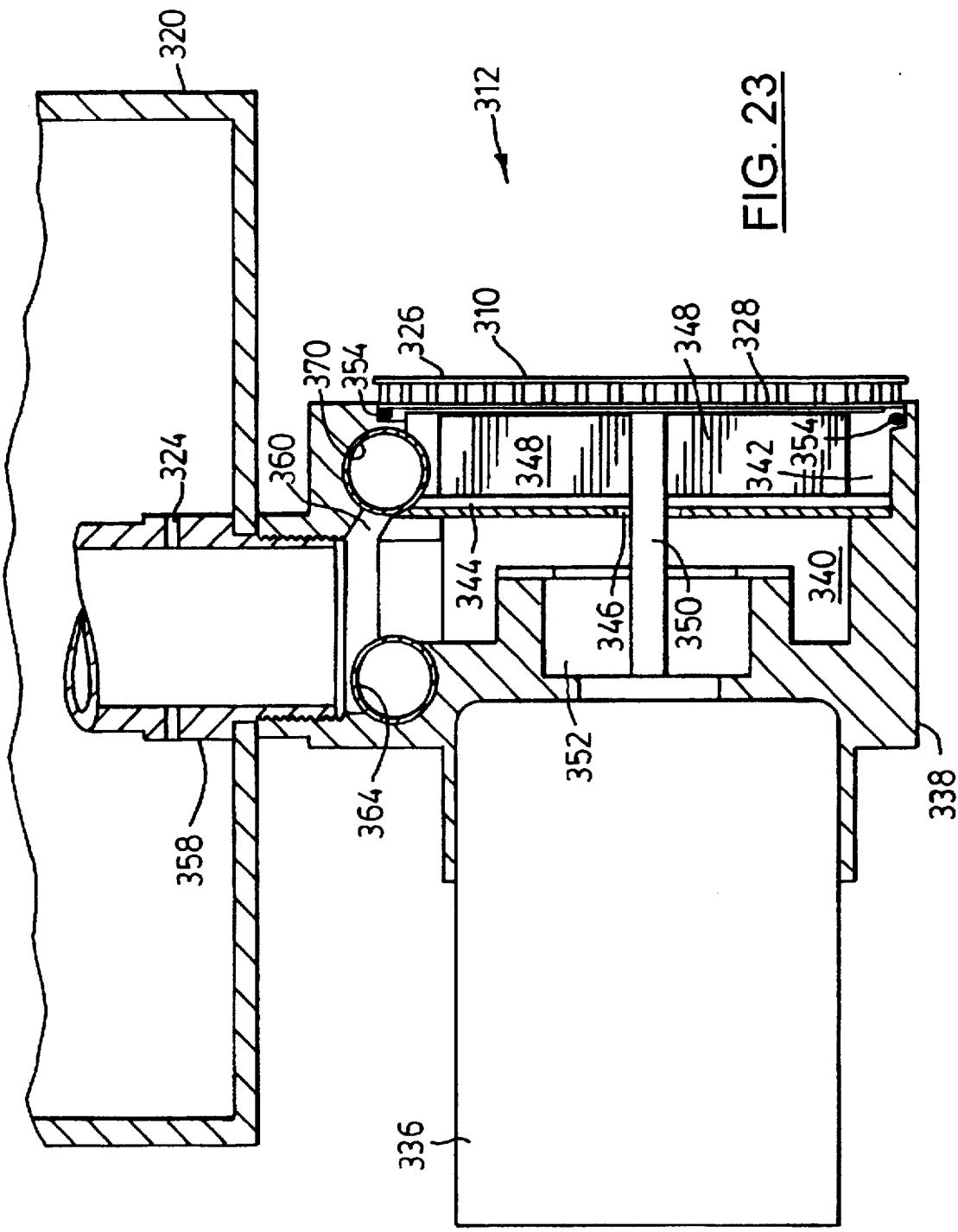
FIG. 23 a sectional view of a water pump forming part of the apparatus of FIG. 22.
Figure 24:
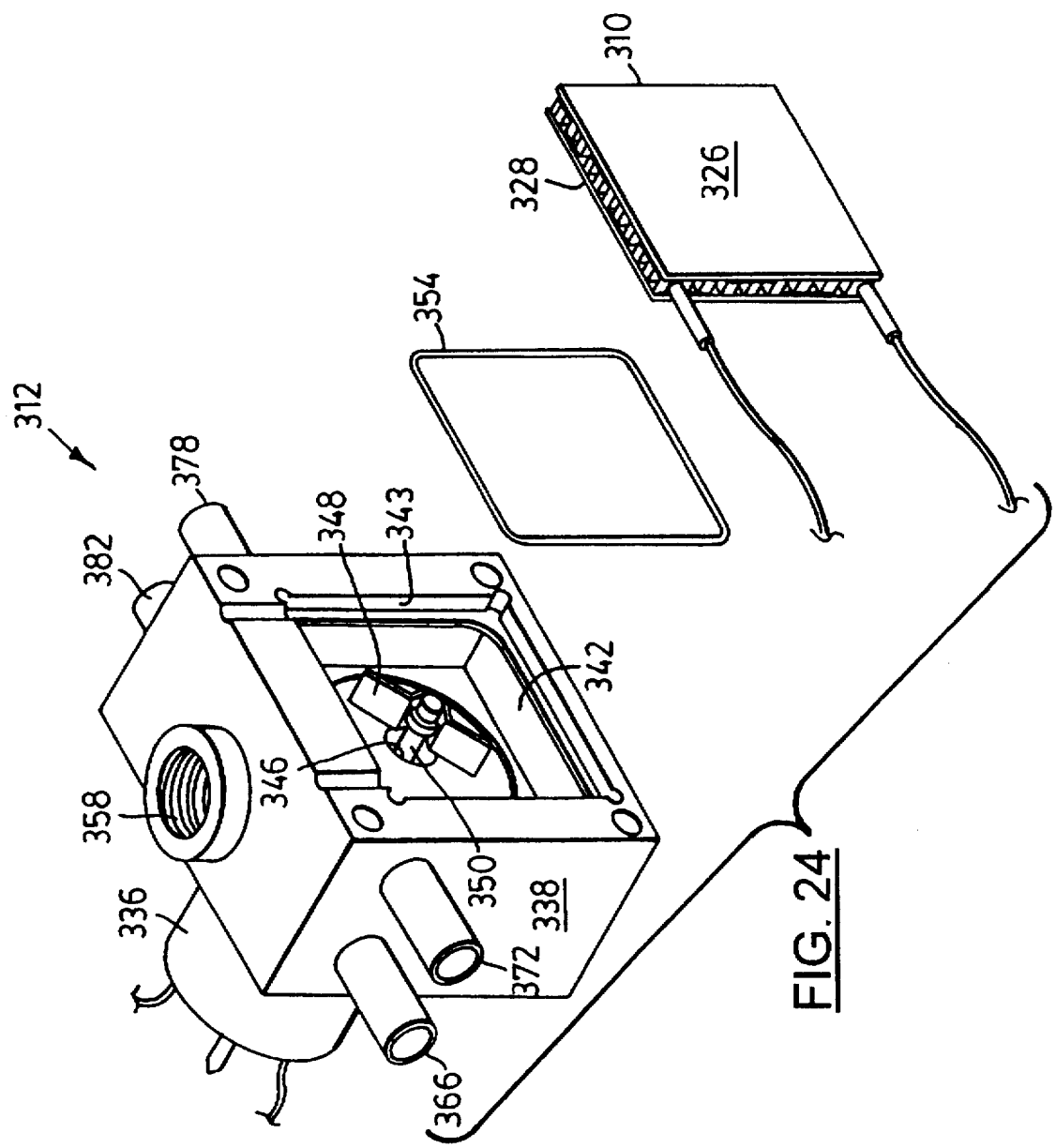
FIG. 24 is an exploded view of a portion of the fluid pump of FIG. 22.

Another embodiment of a cooling device is shown in FIGS. 22 to 24. Referring first to FIG. 22, a heating and cooling device constructed in accordance with the present invention is shown at 300. Apparatus 300 is a table top plug-in unit which operates with between 50 to 200 watts input power and provides a larger surface area pad 302 having a heated section 304 adjacent to a cooled section 306. A power supply 308 provides power through electrical leads 315 to a thermoelectric unit 310 located between two identical water pumps 312 and 314. Pump 312 through which the heated water flows is in flow communication with a heat exchanger 316 provided with a fan 318 for dissipating excess heat. Power supply 308 provides power to fan 318 through leads 319. Water is supplied to the hot and cold sides from a water tank 320 and a microprocessor (not shown) may be integrated into the system for temperature control.

FIGS. 23 and 24 show in greater detail the hot side of the water pump system comprising pump 312 having a motor housing 336, and a housing 338 attached to motor housing 336. Housing 338 defines a first chamber 340 and an impeller enclosure 342. Chamber 340 is separated from impeller enclosure 342 by a disc 344 having a central aperture 346 to provide a fluid flow pathway between chamber 340 and impeller enclosure 342. Housing 338 has an open end portion 343 (FIG. 24) into enclosure 342 and thermoelectric unit 310 is attached to housing 338 at open end portion 343. Side 326 of thermoelectric unit 310 is cooled and side 328 is heated when the current is switched on. Pump 312 includes an impeller 348 mounted for rotation on a motor shaft 350 which passes through a seal 352 into housing 338 where it is connected to the motor.

Impeller 348 is spaced from surface 328 of the thermoelectric unit by about 1 mm, best seen in FIG. 23. An O-ring 354 between thermoelectric unit 310 and housing 338 provides a water seal.

Referring again to FIG. 22, the fluid flow system includes a large water inlet tube 358 to introduce water from tank 320 into first chamber 340 in housing 338. This inlet allows for cross-flow exchange of liquid and air but does not provide recirculation. Referring now to FIG. 23, an air escape passageway 360 extending from enclosure 342 to the interior of tube 358 is provided for exhausting trapped air or allowing air to vent out of the pump 312 thereby permitting the system to automatically prime and provide a static pressure on the system. Passageways 364 extend through the side walls of housing 338 which provide fluid flow communication between first chamber 340 and tubes 366 and 382 shown in FIG. 24. Similarly, passageways 370 seen in FIG. 23 extend through the side walls of housing 338 to provide fluid flow communication between impeller enclosure 342 and water outlet tubes 372 and 378 most visible in FIG. 24.

With reference to FIG. 22, water inlet tubes 358 extend up through the bottom of tank 320 and each has an end portion 322 which is spaced above the water level. Tubes 358 are provided with holes 324 just above the bottom of tank 320, more clearly visible in FIG. 23. Water flows through from tank 320 down through holes 324 into inlet tubes 358 into first chamber 340, through passageway 346 into impeller enclosure 342 and passes over heated/cooled surfaces 328 and 326 respectively of thermoelectric unit 310 and out of water outlet tubes 372. This water flow system, comprising inlet tube 358, chamber 340, enclosure 342, air exhaust 360 and recirculation tubes 366, 372, 378 and 382 provides for cross-flow exchange of liquid and air but does not provide for recirculation between tank 320 and the pumps.

When device 300 is assembled as shown in FIG. 22, pump 314 is attached adjacent to side 326 of thermoelectric unit 310 and the pump is essentially identical to pump 312 just described above and water circulated over surface 326 of the thermoelectric unit is cooled except when the water does not pass through heat exchanger 316. Tubes 378 and 382 on one side of pump 312 conduct heated water to heat exchanger 316 while for the cooled side with pump 314 the corresponding recirculation tubes (not shown) would not be used. Tubes 366 and 372 on the other side of pump 312 recirculate heated water to and from heated section 304 of water bag 302 and the corresponding tubes 366' and 372' on pump 314 recirculate cold water to and from the cooled section 306 of pad 302.

The configuration of pumps 312 and 314 each with impeller 348 located adjacent to opposite sides of thermoelectric unit 310 is very advantageous in that it provides significantly more efficient heat transfer between the thermoelectric unit and the water compared to previous designs in which the pump is spaced away from the water heater and/or water cooler. Rotating impeller 348 right adjacent to the surface of thermoelectric module 310 provides enhanced heat transfer (fluid shear against the heated/cooled surface) into the fluid thereby increasing the efficiency and cooling power over prior art devices. The centrifugal effect created by the rotation of the impeller acts to create a pressure differential to give a pumping action useful for mixing the heat transfer liquid and for pumping the fluid through the systems to the components being cooled and heated. Using a single thermoelectric unit 310 to both heat and cool the water with pumps 312 and 314 mounted on either side of the unit provides a more compact system.

In a preferred embodiment of heating and cooling device 300 thermoelectric unit 310 is a Melcor CP 1.4-127-045L or similar device rated at 120 Watts with 15 Volts and 8 amps and a DC motor used to drive impeller 348 operates at 15 Volts below one ampere.

With appropriate selection of power levels and components such as heat exchanger 316 the water heating and cooling may be provided within safe physiological limits without the need for sophisticated and costly temperature and feedback control systems. Flexible pad 302 may be secured to any part of the body using tape, VELCRO™ straps and the like and may be readily deformed to fit the contours of the body. Apparatus 300 may be modified so that the hot and cold sections 304 and 306 of water bag 302 are periodically switched to provide temporal temperature modulation in addition to spatial temperature modulation. This may be done for example by connecting a heat exchanger and fan to pump 314 so that the hot and cold sides of the apparatus are mirror images of each other. Then the hot and cold sides may be rapidly switched by means of a four way ball valve used to redirect and interchange the hot and cold fluid paths.

Another embodiment of the system may be provided which uses air cooling to cool the hot side of unit thermoelectric unit 310 (not shown).

FIGS. 25 to 29 illustrate an alternative embodiment of a cooling module 400 which may be used in the hot/cold therapy device of FIG. 22. Module 400 includes a housing 402 comprising two matching sections 404 and 406 with section 404 provided with fluid flow passageways 410 and 412 and section 406 provided with passageways 414 and 416. A spigot 418 is attached to the housing at one end of channel 410 and a spigot 424 is attached at the other end. Similar spigots are located at the ends of channel 414. Each section 404 and 406 is provided with an inner O-ring groove 422 each to receive therein a separate O-ring 420 and each housing section defines an inner surface 408 sealed by the O-rings when the unit is assembled as in FIG. 26a. Sandwiched between sections 404 and 406 is a thermoelectric unit 426 having two opposed surfaces 428 and 430 wherein one is heated and the other cooled when a voltage is applied across the unit. When the cooling unit is assembled together with the thermoelectric unit 426, a gap 432 exists between inner surfaces 408 and the opposing surface of the thermoelectric unit. Pump motors 436 are each provided with an impeller housing 438 housing an impeller (not shown) and the impeller housing of two pumps are inserted into channels 412 and 416 and sealed by O-rings 442, best seen in FIG. 25. Each pump 436 has an outlet spigot 440 to which a water hose is connected which connects the unit to the cooling/heating blanket and/or a heat exchanger (not shown).

Figure 25:
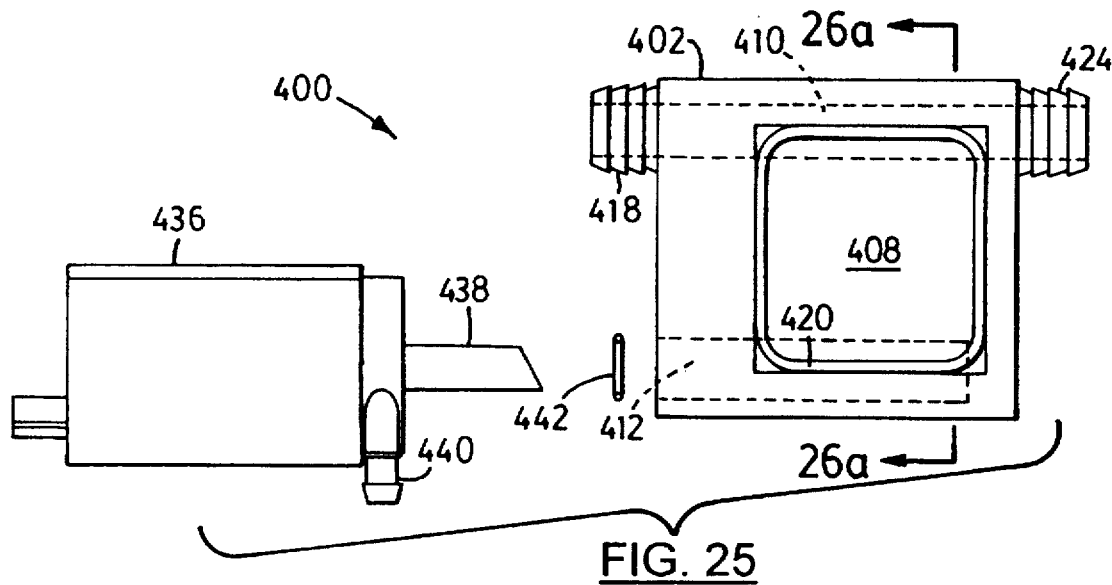
FIG. 25 is an assembly view of an alternative embodiment of a heating/cooling module constructed in accordance with the present invention.
Figure 26A:
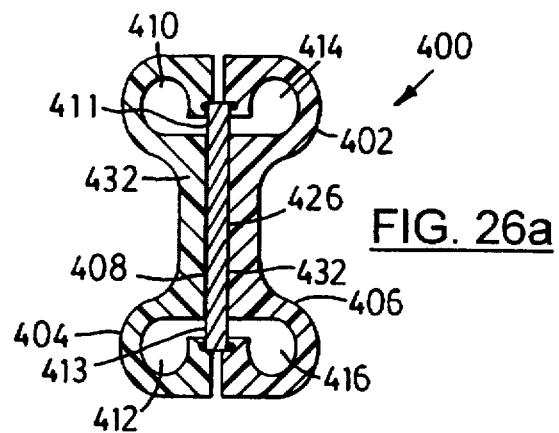
FIG. 26a is a cross sectional view taken along line 26a—26a in FIG. 25.
Figure 26B:
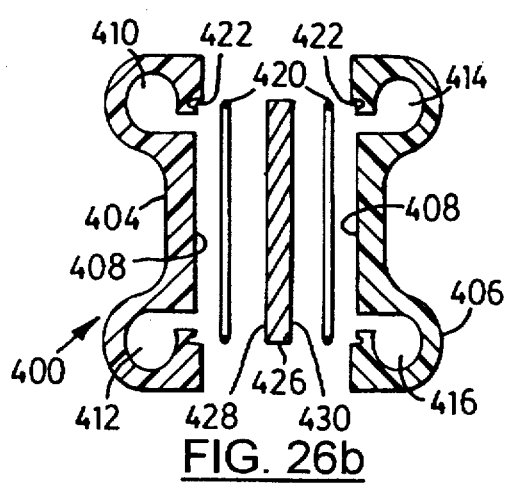
Figure 26C:
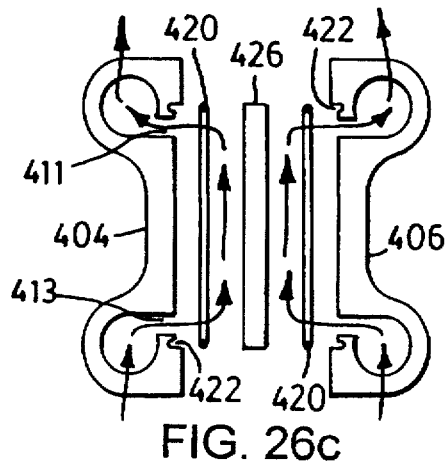
FIG. 26c is similar to FIG. 26b showing the fluid flow path.
Figure 27:
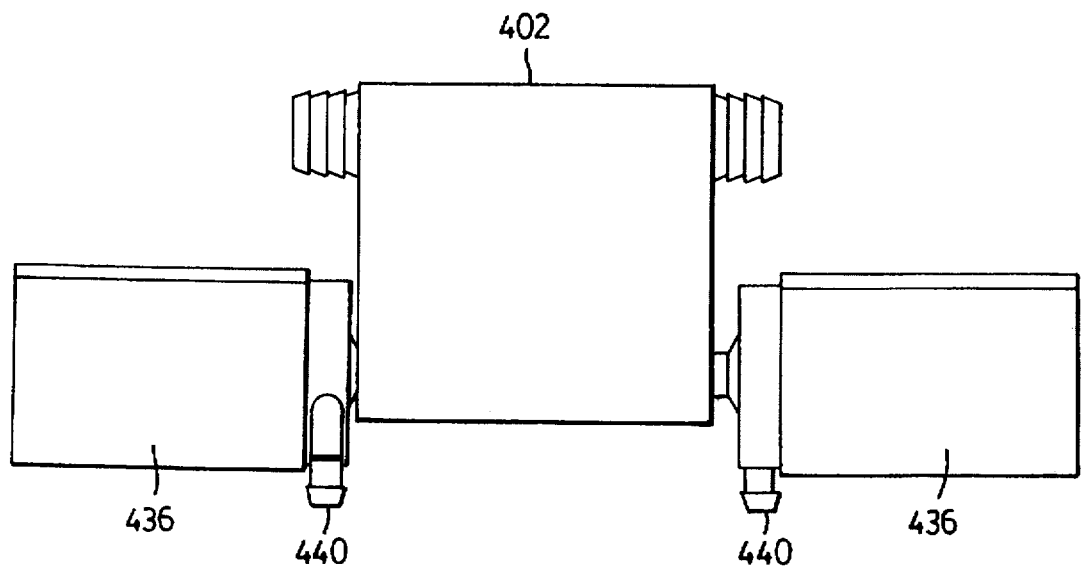
FIG. 27 shows the assembled cooling module of FIGS. 25.
Figure 28:
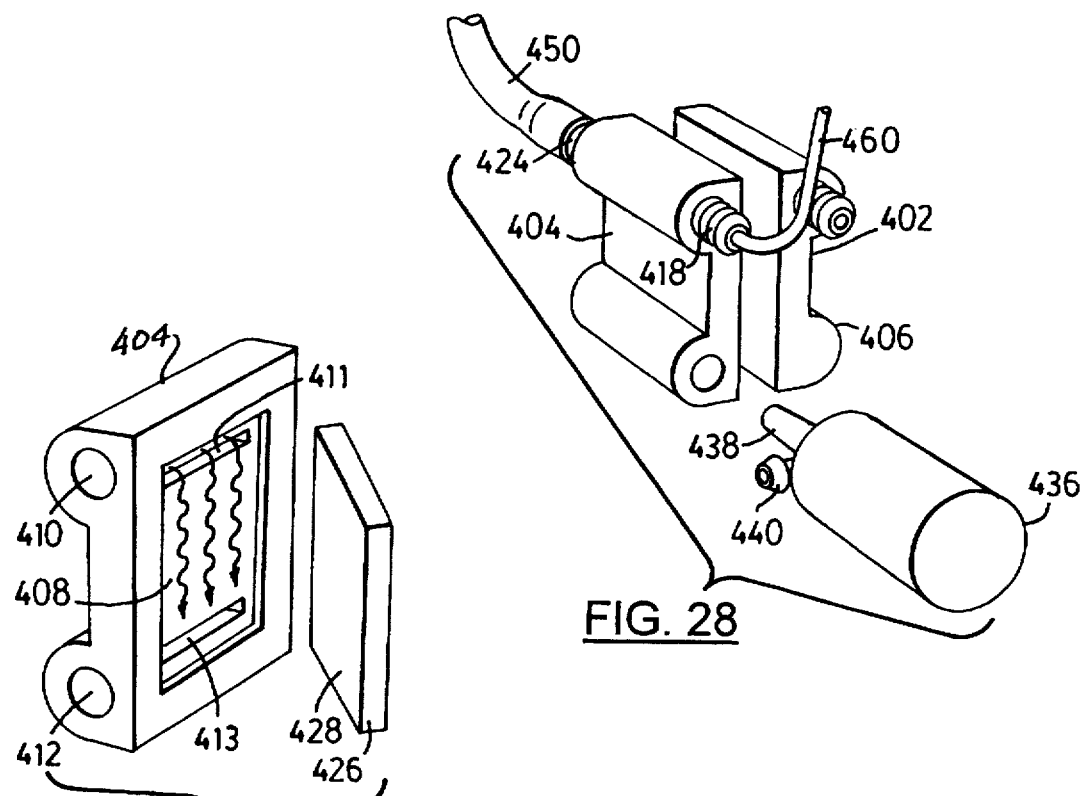
FIG. 28 is a perspective view of a the cooling module of FIG. 25 disassembled.
Figure 29:
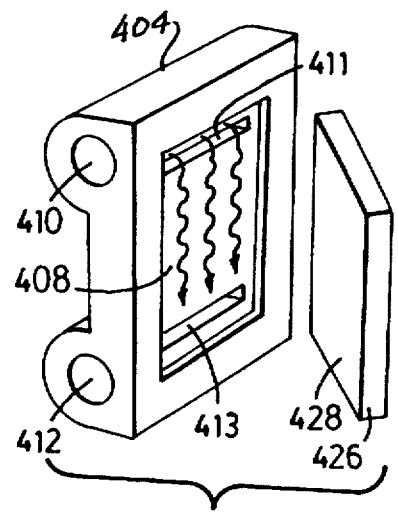
FIG. 29 is a perspective view of part of the cooling module of FIG. 26.

With reference to FIG. 25, fluid returns from the patient blanket (not shown) into spigot 418 through hose 460. Air bubbles are separated and return to the fluid reservoir (not shown) through spigot 424 and air return line 450 attached to the spigot (FIG. 28). Fluid is drawn across the surface 428 of the module 426. The gap 432 between housing surface 408 and module surface 428, best seen in FIG. 26a, is small enough to ensure the shear force of the water breaks the layer of water resting against the module surface and maximizes heat transfer. The refrigerant is cooled as it is uniformly drawn over the surface 428 of module 426 into channel 412 where it is drawn into pump 436 and returned to the patient blanket via pump outlet 440. Fluid returning from the blanket through hose 460 into spigot 418 is allowed to fill reservoir 410 with sufficient fluid so as to provide a uniform flow across the entire cooled surface 428 (FIG. 26c) of thermoelectric Peltier unit 426 to maximize cooling of the fluid. The fluid contacts surface 428 at entry gap 411 and is drawn across the surface 428 and exits through exit gap 413 into reservoir or channel 412, see FIGS. 26a and 29. In this way the refrigerant is vigorously flowed across the cooled surface.

In all the cooling modules disclosed herein the significant improvement in cooling efficiency is achieved by flowing the refrigerant directly and vigorously across the cooled surface of the refrigeration unit. The cooling module of FIG. 5 achieves this by the impeller 164 being spaced from cooled surface 150 of thermoelectric unit 148 on the inside of chamber 112 with refrigerant being circulated across the chamber and up into impeller housing 162 and out through exit port 166. The cooling module of FIG. 24 achieves vigorous flow across surface 328 of thermoelectric unit 326 by rotating in a plane parallel surface 328 a short distance away from the surface. Thus, it will be appreciated that suitable placement of the pump to achieve good flow across the cooled surface is important for realizing the benefits of this invention.

Therefore, while the devices for producing hot and/or cold wraps for alleviating pain has been described and illustrated with respect to the preferred and alternative embodiments, it will be appreciated by those skilled in the art that numerous variations of the invention may be made which still fall within the scope of the invention described herein.

Therefore what is claimed is:

1. A portable therapeutic heat exchange device, comprising:
   a) heat exchange pad means having at least one fluid inlet and one fluid outlet through which a fluid exchange medium may be circulated through said pad means; and
   b) a heat exchange module including a first housing, said first housing having a fluid recirculation inlet and a fluid recirculation outlet and conduit means communicating said recirculating fluid inlet and said recirculating fluid outlet with said fluid outlet and fluid inlet, respectively, of said pad means, a first chamber within said first housing in fluid communication with a source of fluid heat exchange medium and said fluid recirculation inlet and said fluid recirculation outlet, at least one opening in said first housing into said first chamber, one of either a heat source and a heat sink having an inner surface mounted within said opening with said inner surface in heat exchange relationship with the fluid heat exchange medium within said first chamber, and means for circulating the fluid heat exchange medium through said first chamber so as to contact said inner surface and to convey the fluid heat exchange medium to said recirculating fluid outlet to said pad means.

2. The heat exchange device according to claim 1 wherein said means for circulating said fluid heat exchange medium is a first pump with a first impeller, said first pump means being in flow communication with said fluid recirculation outlet to pump said fluid heat exchange medium out of said first chamber.

3. The heat exchange device according to claim 2 wherein said one of either a heat source and heat sink is a thermoelectric Peltier unit comprising said inner surface and an opposed outer surface, said pump being attached to said first housing with the first impeller located in said first chamber spaced from said inner surface.

4. The heat exchange device according to claim 3 wherein said source of fluid heat exchange medium is a reservoir having an entrance and exit port, said exit port in flow communication with said entrance port of said first housing.

5. The heat exchange device according to claim 4 wherein during operation said inner surface of said thermoelectric Peltier unit is cooled and said outer surface is heated, including a heat exchanger for dissipating heat produced by said outer surface, and wherein said heat exchanger thermally communicates with said heated surface.

6. The heat exchange device according to claim 5 wherein said heat exchanger includes a heat exchanger chamber, a thermally conducting solid portion adjacent to said heat exchanger chamber and a finned portion extending from said solid portion, and wherein said first housing is seated in said heat exchanger chamber with said heated surface thermally contacted to said solid portion.

7. The heat exchange device according to claim 6 wherein said heat exchanger chamber has a shape defined by at least one pair of opposed walls, said heat exchanger including a thermally conducting solid portion adjacent to each of said at least one pair of opposed walls, said first housing having a shape complementary to said shape of said heat exchanger chamber with said first chamber having a number of open end portions equal to said walls and a thermoelectric Peltier unit sealingly engaged in each opening.

8. The heat exchange device according to claim 7 wherein said heat exchanger has a top and a bottom and said heat exchanger chamber is tapered from the top to the bottom, and wherein said first housing has a taper substantially matching the taper in said heat exchanger chamber so that when said cooling module is inserted into said heat exchanger chamber said thermoelectric Peltier units are sandwiched between said first housing and said wall of said heat exchanger chamber.

9. The heat exchange device according to claim 8 wherein said heat exchanger comprises a plurality of heat exchange plates assembled in a stacked relationship to define said heat exchanger.

10. The heat exchange device according to claim 9 wherein each heat exchanger plate has an enlarged central section with sides and fin portions extending from said sides.

11. The heat exchange device according to claim 10 wherein said central section of each planar element has an aperture, and wherein in said stack said central sections of adjacent planar members are partially overlapped to form said thermally conducting solid portion with the apertures in registration to define walls of said heat exchanger chamber.

12. The heat exchange device according to claim 11 wherein the fin portions are provided with dimples extending transversely to said fin portions, and wherein adjacent fin portions in said stack are spaced from each other by said dimples to provide an air gap between adjacent fin portions.

13. The heat exchange device according to claim 12 in which said stacked plates include at least one secondary opening therein, and fan means mounted within said at least one secondary opening for circulating air between said fin portions.

14. The heat exchange device according to claim 3 including a heat exchange means mounted in fluid communication with said outer surface of said thermoelectric Peltier unit.

15. The heat exchange device according to claim 14 including a second housing having a second chamber with an entrance in fluid communication with said source of fluid heat exchange medium, said second housing having a fluid recirculating inlet and a fluid recirculating outlet communicating with said second chamber, at least one opening in said second housing communicating with said second chamber, said second housing being mounted relative to said first housing such that said outer surface of said thermoelectric Peltier unit is in fluid communication at said at least one opening into said second housing with said second chamber so that the fluid heat exchange medium in said first housing is cooled and said fluid heat exchange medium in said second housing is heated.

16. The heat exchange device according to claim 15 wherein said conduit means includes first fluid circulating lines connecting to a first fluid inlet and outlet of a first cooled section of said heat exchange pad means to said fluid recirculating inlet and outlet of said first housing and second fluid circulating lines connecting a second fluid inlet and outlet of a second cooled section of said heat exchange pad means to said fluid recirculating inlet and outlet of said second housing, including means for circulating the fluid heat exchange medium through said second chamber so as to contact said outer surface and to convey the fluid heat exchange medium to said recirculating fluid outlet to said pad means.

17. The heat exchange device according to claim 16 wherein said first pump has a first pump motor and a first pump shaft extending from the pump motor, said first impeller is an elongate first impeller mounted on said first pump shaft for rotation about said first pump shaft adjacent to said inner surface so that during rotation said elongate first impeller rotates substantially parallel to said inner surface, and wherein said means for circulating the fluid heat exchange medium through said second chamber is a second pump having a second pump motor and a second pump shaft extending from said second pump motor, an elongate second impeller mounted on said second pump shaft for rotation about said second pump shaft adjacent to said outer surface so that during rotation said elongate second impeller rotates substantially parallel to said outer surface.

18. The heat exchange device according to claim 17 wherein said first housing has a pump housing enclosing a first impeller chamber in flow communication with said first chamber through a first restricted passageway, said first pump has a first pump motor, said first impeller is an elongate first impeller extending from said first pump motor and located in said first impeller chamber, and wherein said second housing has a pump housing enclosing a second impeller chamber in flow communication with said second chamber through a second restricted passageway, and wherein said means for circulating the fluid heat exchange medium through said second chamber is a second pump having a second pump motor and an elongate second impeller extending from said second pump motor and located in said second impeller chamber.

19. The heat exchange device according to claim 18 wherein the recirculation inlet on said first housing includes an inlet housing enclosing an inlet reservoir in flow communication with said first chamber through a third restricted passageway, the inlet housing being spaced from said impeller housing, and wherein the recirculation inlet on said second housing includes an inlet housing enclosing an inlet reservoir in flow communication with said second chamber through a fourth restricted passageway.

20. The heat exchange device according to claim 5 including a flow sensor for sensing fluid flow rate in the fluid circulation inlet.

21. The heat exchange device according to claim 5 wherein said reservoir is mounted above said heat exchanger, an outer housing being attachable to said heat exchanger, said housing having a top and sides, and a carrying handle attached to said top.

22. The heat exchange device according to claim 21 wherein said reservoir is made of a translucent plastic.

23. The heat exchange device according to claim 22 wherein said reservoir has a lid covering said entrance of said reservoir, said lid having at least one pin hole for passage of air into and out of said reservoir.

24. The heat exchange device according to claim 23 wherein said reservoir includes an air return spigot, an air return line attached to said air return spigot, the housing including an air escape vent communicating with said first chamber, the air escape vent being connected to said air return line so that air is displaced out of the first chamber into the reservoir.

25. The heat exchange device according to claim 24 wherein said air return spigot is located in a top portion of a wall of said reservoir, the reservoir being provided with a web projecting downwardly from said top portion spaced from said air return spigot to thereby define an air gap adjacent said air return spigot.

26. The heat exchange device according to claim 22 wherein said outer housing is provided with hook means extending outwardly therefrom.

27. A portable therapeutic heat exchange device, comprising:
a) heat exchange pad means having at least one fluid inlet and one fluid outlet through which a fluid exchange medium may be circulated through said pad means;
b) a heat exchange module including a housing having a fluid recirculation inlet and a fluid recirculation outlet and conduit means communicating said recirculating fluid inlet and said recirculating fluid outlet with said fluid outlet and fluid inlet, respectively, of said pad means, a chamber within said housing in fluid communication with a source of fluid heat conducting medium and said fluid recirculation inlet and said fluid recirculation outlet, at least one opening in said housing into said chamber, a thermoelectric Peltier unit having a heated outer surface and a cooled inner surface mounted within said opening with said cooled inner surface in heat exchange relationship with the fluid heat exchange medium within said chamber, and means for circulating the fluid heat exchange medium through said chamber so as to contact said cooled inner surface and to convey the fluid heat exchange medium to said recirculating fluid outlet to said pad means; and
c) a heat exchanger with a heat exchanger chamber, a thermally conducting solid portion adjacent to said chamber and a finned portion extending from said solid portion, and wherein said cooling module is seated in said heat exchanger chamber with said outer heated surface thermally contacted to said solid portion.

28. The heat exchange device according to claim 27 wherein said means for circulating said fluid heat exchange medium is a pump with an impeller, said pump being attached to said first housing with the first impeller located in said first chamber spaced from said inner surface.

29. The heat exchange device according to claim 28 wherein said heat exchanger chamber has a shape defined by at least one pair of opposed walls, said housing having a shape complementary to said shape of said heat exchanger chamber with said housing having a number of openings equal to said walls and a thermoelectric Peltier unit mounted in each opening in sealing relationship with said housing.

30. The heat exchange device according to claim 29 wherein said heat exchanger has a top and a bottom and said heat exchanger chamber is tapered from the top to the bottom, and wherein said housing has a taper substantially matching the taper in said heat exchanger chamber so that when said cooling module is inserted into said heat exchanger chamber said thermoelectric Peltier units are sandwiched between said housing and said wall of said heat exchanger chamber.

31. The heat exchange device according to claim 30 wherein said heat exchanger comprises a plurality of heat exchange plates assembled in a stacked relationship to define said heat exchanger.

32. The heat exchange device according to claim 31 wherein each heat exchanger plate has an enlarged central section with sides and fin portions extending from said sides.

33. The heat exchange device according to claim 32 wherein said central section of said heat exchange plates have an aperture, and wherein said central sections of adjacent plates are partially overlapped to form said thermally conducting solid portion with the apertures in registration to define walls of said heat exchanger chamber.

34. The heat exchange device according to claim 33 wherein the fin portions are provided with dimples extending transversely to said fins, and wherein adjacent fin portions in said stack are spaced from each other by said dimples to provide an air gap between adjacent fin portions.

35. The heat exchange device according to claim 34 in which said stacked plates include at least one secondary opening therein, and fan means mounted within said at least one secondary opening for circulating air between said fin portions.

36. The heat exchange device according to claim 28 wherein said source of fluid heat exchange medium is a reservoir having a fluid containing volume and an entrance and exit port for said fluid heat exchange medium, said exit port in flow communication with said entrance port of said housing, said housing having a volume substantially smaller than said chamber within said housing.

37. The heat exchange device according to claim 29 including a flow sensor for sensing fluid flow rate in the fluid circulation inlet.

38. The heat exchange device according to claim 29 wherein said reservoir is mounted above said heat exchanger, an outer housing being attachable to said heat exchanger, said housing having a top and sides, and a carrying handle attached to said top.

39. The heat exchange device according to claim 38 wherein said reservoir is made of a translucent plastic, wherein said reservoir has a lid covering said entrance of said reservoir, said lid having at least one pin hole for passage of air into and out of said reservoir.

40. The heat exchange device according to claim 39 wherein said reservoir includes an air return spigot, an air return line attached to said air return spigot, the housing including an air escape vent communicating with said module chamber, the air escape vent being connected to said air return line so that air is displaced out of the chamber into the reservoir.

41. The heat exchange device according to claim 39 wherein said outer housing is provided with hook means extending outwardly therefrom.

42. A compact heat exchange device for cooling and/or heating a heat exchange fluid, comprising:

a) a heat exchange module including a first housing having a fluid recirculation inlet and a fluid recirculation outlet, a first chamber within said first housing in fluid communication with said fluid recirculation inlet and said fluid recirculation outlet, at least one opening in said first housing into said first chamber, a thermoelectric Peltier unit having a first surface and an opposed second surface, the thermoelectric Peltier unit being mounted within said opening in liquid tight sealing relationship with said housing with said first surface in heat exchange relationship with a fluid heat exchange medium within said first chamber; and b) a first pump with a first impeller, said first pump being attached to said first housing in communication with said fluid recirculation outlet to pump for circulating the heat exchange fluid through said first chamber so as to contact said first surface and to convey the heat exchange fluid through said recirculating fluid outlet.

43. The device according to claim 42 wherein said first pump is attached to said first housing with the first impeller located in said first chamber spaced from said first surface.

44. The device according to claim 43 including a second housing having a second chamber and a fluid recirculating inlet and a fluid recirculating outlet communicating with said second chamber, at least one opening in said second housing communicating with said second chamber, said second housing being mounted relative to said first housing such that said second surface of said thermoelectric Peltier unit is in fluid communication at said at least one opening into said second housing with said second chamber and in liquid tight sealing relationship with said second chamber, a second pump with a second impeller, said second pump being attached to said second housing in communication with said fluid recirculation outlet for circulating the heat exchange fluid through said second chamber so as to contact said second surface and to convey the heat exchange fluid through said recirculating fluid outlet.

45. The device according to claim 44 wherein said first pump has a first pump motor and a first pump shaft extending from the pump motor, said first impeller is an elongate first impeller mounted on said first pump shaft for rotation about said first pump shaft adjacent to said first surface so that during rotation said elongate first impeller rotates substantially parallel to said first surface, and wherein said second has a second pump motor and a second pump shaft extending from said second pump motor, an elongate second impeller mounted on said second pump shaft for rotation about said second pump shaft adjacent to said second surface so that during rotation said elongate second impeller rotates substantially parallel to said second surface.

46. The device according to claim 44 wherein said first housing has a pump housing enclosing a first impeller chamber in flow communication with said first chamber through a first restricted passageway, said first pump has a first pump motor, said first impeller is an elongate first impeller extending from said first pump motor and located in said first impeller chamber, and wherein said second housing has a pump housing enclosing a second impeller chamber in flow communication with said second chamber through a second restricted passageway, and wherein said means for circulating the fluid heat exchange medium through said second chamber is a second pump having a second pump motor and an elongate second impeller extending from said second pump motor and located in said second impeller chamber.

47. The device according to claim 46 wherein the recirculation inlet on said first housing includes an inlet housing enclosing an inlet reservoir in flow communication with said first chamber through a third restricted passageway, the inlet housing being spaced from said impeller housing, and wherein the recirculation inlet on said second housing includes an inlet housing enclosing an inlet reservoir in flow communication with said second chamber through a fourth restricted passageway.

* * * * *